US005876967A

United States Patent [19]

Nathans et al.

[11] Patent Number: 5,876,967

[45] Date of Patent: Mar. 2, 1999

[54] FIBROBLAST GROWTH FACTOR HOMOLOGOUS FACTOR-2 AND METHODS OF USE

[75] Inventors: Jeremy Nathans, Baltimore; Philip M. Smallwood, Woodbine; Jennifer P. Macke, Columbia, all of Md.

[73] Assignee: The Johns Hopkins University School of Medicine, Baltimore, Md.

[21] Appl. No.: 438,439

[22] Filed: May 12, 1995

[51] Int. Cl.$^6$ .................. C12N 15/00; C12N 15/63; C12N 15/82; C07H 21/04

[52] U.S. Cl. .................. 435/69.4; 435/69.1; 435/90.2; 435/252.3; 435/320.1; 536/23.5; 536/23.51; 935/23; 935/69; 935/70; 935/71; 935/72

[58] Field of Search .................. 536/23, 51, 23.5; 935/23, 69–72; 435/69.1, 320.1, 252.3, 240.2, 69.4

[56] References Cited

PUBLICATIONS

Adams M D; Soares M B; Kerlavage A R; Fields C; Venter J C. Rapid cDNA sequencing (expressed sequence tags) from a directionally cloned human infant brain cDNA library. Nature Genetics, (1993 Aug.) 4 (4) 373–80.

Molecular Cloning A Laboratory Manual. Second Edition vols. 1 2 and 3. Sambrook J; Fritsch E F; Maniatis T. Cold Spring Harbor Laboratory Press; Cold Spring Harbor, New York, USA, Chapter 11, p. 47, Nov. 1989.

Methods in Enzymology, vol. 152, Guide to Molecular Cloning Techniques. Berger et al, ed. Academic Press, New York, NY. 1987, Chapter 47, pp. 432–443, Jun. 1988.

Journal of Cellular Physiology, vol. 162 No. 3 Mar 1995 Quantitative Export of F6F-2 occurs Through an Alternative, Energy–Dependent, Non–ER/Golgi Pathway, pp. 388–399.

Development vol. 118 1993 pp. 95–104 Retroviral expression of F6F-2 (6FGF) affects patterning in chick limb bud.

Febs letters, vol. 349 3 Jun. 1994, Purification and Characterization of 210–amino acid recombinant basic fibroblast growth factor form (F6F-2).

Cell Growth and Differentiation, vol. 2 No. 11 Nov. 1991, Production and Functional Characterization of Human Recombinant F6F–6 Protein.

*Primary Examiner*—Elizabeth C. Kemmerer
*Assistant Examiner*—David S. Romeo
*Attorney, Agent, or Firm*—Fish & Richardson, P.C.

[57] ABSTRACT

A novel growth factor, fibroblast growth factor homologous factor-2 (FHF-2) polypeptide, the polynucleotide sequence encoding FHF-2 and the deduced amino acid sequence are disclosed. Also disclosed are diagnostic and therapeutic methods of using the FHF-2 polypeptide and polynucleotide sequences and antibodies which specifically bind to FHF-2.

10 Claims, 6 Drawing Sheets

```
GAATTCCGCT TGCACAGTGT CCGCCGGGCG CAGGGGCCGA CCGCACGCAG TGCGCAGTT   60

CTGCCTCCGC CTGCCAGTCT CGCCCGCGAT CCCGGCCCGG GGCTGTGGCG TCGACTCCGA  120

CCCAGGCAGC CAGCAGCCCG CGCGGGAGCC GGACCGCCGC CGGAGAGCTC GGACGGCATG  180

CTGAGCCCCC TCCTTGGCTG AAGCCCGAGT GCGGAGAAGC CCGGGCAAAC GCAGGCTAAG  240

GAGACCAAAG CGGCGAAGTC GCGAGACAGC GGACAAGCAG CGGAGGAGAA GGAGGAGGAG  300

GCGAACCCAG AGAGGGGCAG CAAAAGAAGC GGTGGTGGTG GGCGTCGTGG CCATGGCGGC  360
                                                         M  A  A

GGCTATCGCC AGCTCGCTCA TCCGTCAGAA GAGGCAAGCC CGCGAGCGCG AGAAATCCAA  420
 A  I  A    S  S  L    I  R  Q  K   R  Q  A    R  E  R   E  K  S  N

CGCCTGCAAG TGTGTCAGCA GCCCCAGCAA AGGCAAGACC AGCTGCGACA AAAACAAGTT  480
 A  C  K    C  V  S    S  P  S  K   G  K  T    S  C  D    K  N  K  L

AAATGTCTTT TCCCGGGTCA AACTCTTCGG CTCCAAGAAG AGGCGCAGAA GAAGACCAGA  540
 N  V  F    S  R  V    K  L  F  G   S  K  K    R  R  R   R  P  E

GCCTCAGCTT AAGGGTATAG TTACCAAGCT ATACAGCCGA CAAGGCTACC ACTTGCAGCT  600
 P  Q  L    K  G  I    V  T  K  L   Y  S  R    Q  G  Y    H  L  Q  L

GCAGGCGGAT GGAACCATTG ATGGCACCAA AGATGAGGAC AGCACTTACA CTCTGTTTAA  660
 Q  A  D    G  T  I    D  G  T  K   D  E  D    S  T  Y    T  L  F  N.

CCTCATCCCT GTGGGTCTGC GAGTGGTGGC TATCCAAGGA GTTCAAACCA AGCTGTACTT  720
 L  I  P    V  G  L    R  V  V  A   I  Q  G    V  Q  T    K  L  Y  L

GGCAATGAAC AGTGAGGGAT ACTTGTACAC CTCGGAACTT TTCACACCTG AGTGCAAATT  780
 A  M  N    S  E  G    Y  L  Y  T   S  E  L    F  T  P    E  C  K  F

CAAAGAATCA GTGTTTGAAA ATTATTATGT GACATATTCA TCAATGATAT ACCGTCAGCA  840
 K  E  S    V  F  E    N  Y  Y  V   T  Y  S    S  M  I    Y  R  Q  Q

GCAGTCAGGC CGAGGGTGGT ATCTGGGTCT GAACAAAGAA GGAGAGATCA TGAAAGGCAA  900
 Q  S  G    R  G  W    Y  L  G  L   N  K  E    G  E  I    M  K  G  N

CCATGTGAAG AAGAACAAGC CTGCAGCTCA TTTTCTGCCT AAACCACTGA AAGTGGCCAT  960
 H  V  K    K  N  K    P  A  A  H   F  L  P    K  P  L    K  V  A  M

GTACAAGGAG CCATCACTGC ACGATCTCAC GGAGTTCTCC CGATCTGGAA GCGGGACCCC 1020
 Y  K  E    P  S  L    H  D  L  T   E  F  S    R  S  G    S  G  T  P

AACCAAGAGC AGAAGTGTCT CTGGCGTGCT GAACGGAGGC AAATCCATGA GCCACAATGA 1080
 T  K  S    R  S  V    S  G  V  L   N  G  G    K  S  M    S  H  N  E

ATCAACGTAG CCAGTGAGGG CAAAAGAAGG GCTCTGTAAC AGAACCTTAC CTCCAGGTGC 1140
 S  T

TGTTGAATTC
```

FIG. 1

```
FGF-8   M SPRSALS- --CLLLHLLV LC----LQAQ- -VTVQSSPN- -------FTQ-         34
FGF-9   M ---APLGE ---VGNYFGVQ DA-----VPF- -GNVPVLPVD ---SPVLLSDH         36
FHF-1   M A--AAIAS SLIRQKRQAR ESNSDRVSA- -SKRRSSPSK --DGRSLCER             43
FGF-1   M -------- ---------- --------AE- -GEITTFTA- -------LTE-           14
FGF-2   M -------- ---------- --------AA- -GSITTLPA- -------LPED          15
FGF-3   M SLIWLLLL- ---SLLEPSW- ---------FT- -TGFGTRLR- -------RDA-        29
FGF-5   M SLSFLLLLF FSHLILSAWA HGEKRLAPKG QPGPAATDRN PIGSSSRQSS           50
FGF-4   M SGPGTAAV- ----ALLPAVLL ALLAPWAGRG GAAAPTAPNG TLEAELERRW         47
FGF-6   M RGAGRLQ- --GTLWA---L VFLGILVGMV VPSPAGTRAN NTLLD-SRGW            44
FGF-7   M -----KWIL- ----TWILPTLL YRSCFHIICL VGTISLACND -------MTPE        38

FGF-8   ---------- -------HVR EQSLVTD--Q LSRRLIRTYQ L SRTS-GKH             64
FGF-9   --LGQ-SEA- --G----GLP RGPAVTDLDH LKGILRRRQ- L YCRT--GFH            73
FHF-1   HVLGVFSKVR FCS----GRK RPVRRRFEPQ LKGIVTR--- L FSQQ--GYF            84
FGF-1   -------K-- --F-----NLP PG-------N YKK-PKL--- L YCSNG-GHF           37
FGF-2   GG-----S-- --G-----AFP PG-------H FKD-PKR--- L YCKNG-GFF           49
FGF-3   ---------- -------GGR GGVYEHLG-- -GAPRRR--K L YC--ATKYH            55
FGF-5   SSAMSSSSAS SSPAASLGSQ GSGLEQSSFQ WSPSGRRTGS L YCRVGIGFH           100
FGF-4   ESLVALSLAR LPVAAQPKEA AVQSGAGDYL LGIKRLR--R L YCNVGIGFH            95
FGF-6   GTL---LSRSR AGLAGE---IA GVNWESG-YL VGIKRQR--R L YCNVGIGFH          87
FGF-7   Q-----MATNV NCS-----SPE RHTRSYDYME GGDIRVR--R L YCRT--QWY          76

FGF-8   VQVLANKRIN AMAEDGDPFA KLIVETDTFG SRVRVRGAET GLYICMNKKG           114
FGF-9   LEIFPNGTIQ GTRKDHSRFG ILEFISIAVG L VSIRGVDS GLYLCMNERG             122
FHF-1   LQMHPDGTID GTKDENSDYT LFNLIPVGLR V VAIQGVKA SLYVAMNGEG             133
FGF-1   LRILPDGTVD GTRDRSDQHI QLQLSAESVG E VYIKSTET GQYLAMDTDG             86
FGF-2   LRIHPDGRVD GVREKSDPHI KLQLQAEERG V VSIKGVCA NRYLAMKEDG             89
FGF-3   LQLHPSGRVN GS-LENSAYS ILEITAVEVG V VAIKGLFS GRYLAMNKRG            103
FGF-5   LQIYPDGKVN GS-HEANMLS VLEIFAVSQG I VGIRGVFS NKFLAMSKKG            148
FGF-4   LQALPDGRIG GA-HADTRDS LLELSPVERG V VSIFGVAS RFFVAMSSKG            143
FGF-6   LQVLPDGRIS GT-HEENPYS LLEISTVERG V VSLFGVRS ALFVAMNSKG            135
FGF-7   LRIDKRGKVK GTQEMKNNYN IMEIRTVAVG I VAIKGVES EFYLAMNKEG            125

FGF-8   R LAKSNGKG R LAPAEIVL ENHYNTYASA KYEG------- --                    148
FGF-9   R LYGSEKLTQ ECVFREQFE ENWYNTYSSN LYKHVD----- ----TGRR              161
FHF-1   R LYSSDVFTP ECKFKESVF ENYYVTYSST LYRQQE----- ----SGRA              172
FGF-1   R LYGSQTPNE ECLFLERLE ENHYNTYISK KHAEKN-----                      121
FGF-2   R LLASKCVTD ECFFFERLE SNNYNTYRSR KYT--S---                        122
FGF-3   R LYASDHYNA ECEFVERIH ELGYNTYASR LYRTGSSGPG AQRQPGAQRP           152
FGF-5   R LYASAKFTD ECKFRERFQ ENSYNTYASA IHRTEKTG-- -----RE               187
FGF-6   R LKGSPFFTD ECTFKEILL PNNYNAYESY KYPGM----- ---                   177
FGF-7   R LYAKPSFQE ECKFRETLL PNNYNAYESD LYQGT----- ---                   169
FGF-7   R LYRKECNE -CYFLEKLIL ENHYNTYASA KWTHNG---- ----GE                162
```

FIG. 2A

```
FGF-8  WIMAFTRQGR  PRQSKTRQH   QREVHFMKRL  PRGHHTTEQS  L----------          189
FGF-9  YYVALNKDGT  PREGTRTKRH   QKFTHFLPRP  VD---------  ----------          193
FHF-1  WFLGLNKEGQ  IMKGNRVKKT   KPSSHFVPKP  IEVC-------  ----------          206
FGF-1  WFVGLRKNGS  CKRGPRTHYG   QKAILFLPLP  VS---------  ----------          153
FGF-2  WYVALKRTGQ  YKLGSKTGPG   QKAILFLPMS  AKS--------  ----------          155
FGF-3  WYVSVNGKGR  PRRGFKTRRT   QKSSLFLERV  LGHKDHEMVR  LLQSSQPRAP          202
FGF-5  WYVALNKRGK  AKRGCSPR---  VK-----PQH  IS--THFLPR  FKQSEQPELS          228
FGF-4  -FIALSKNGK  TKKGNRVS---  -------PTM  KV--THFLPR  L---------          206
FGF-6  -YIALSKYGR  VKRGSKVS---  -------PIM  TV--THFLPR  I---------          198
FGF-7  MFVALNQKGI  PVRGKKTKKE   QKTAHFLPMA  IT---------  ----------          194

FGF-8  ----------  --------RFE  FLNYPPFTRS  LRGSQRTWAP  EPR                 216
FGF-9  ----------  P-------DK-  --------VP  ELYKD-ILSQ  S--                 208
FHF-1  ------MYRE  PSLHEIGEKQ   GRSRKSSGTP  TMNGGKVVNQ  DST                 243
FGF-1  ----------  ----------   ----------  -------SD-  ---                 155
FGF-2  ----------  ----------   ----------  ----------  ---                 155
FGF-3  GEGSQPRQRR  QKKQSPGDHG   KMETLSTRAT  PSTQLHTGGL  AVA                 245
FGF-5  FTVTVP---E  KKNPPSPIKS   KIPLSAPRKN  TNSVKYRLKF  RFG                 268
FGF-4  ----------  ----------   ----------  ----------  ---                 206
FGF-6  ----------  ----------   ----------  ----------  ---                 198
FGF-7  ----------  ----------   ----------  ----------  ---                 194
```

FIG. 2B

FIBROBLAST GROWTH FACTOR HOMOLOGOUS FACTOR-2 AND METHODS OF USE

BACKGROUND OF THE INVENTION

1. Field Of The Invention

The invention relates generally to growth factors and specifically to a novel member of the fibroblast growth factor family, denoted fibroblast growth factor homologous factor-2 (FHF-2) and the polynucleotide encoding FHF-2.

2. Description Of Related Art

The fibroblast growth factor family encompasses a group of structurally related proteins with a wide range of growth promoting, survival, and/or differentiation activities in vivo and in vitro (reviewed in Baird, A., and Gospodarowicz, D. *Ann N.Y. Acad. Sci.* 638: 1, 1991; Eckenstein, F. P., *J.Neurobiology* 25: 1467, 1994; Mason, I.J. *Cell* 78: 547, 1994). As of December 1994, nine members of this family had been characterized by molecular cloning. The first two members of the family to be characterized, acidic fibroblast growth factor (aFGF/FGF-1) and basic fibroblast growth factor (bFGF/FGF-2), have been found in numerous tissues, including for example brain, eye, kidney, placenta, and adrenal (Jaye et al., *Science* 233: 541, 1986; Abraham et al., *Science* 233: 545, 1986). These factors have been shown to be potent mitogens and survival factors for a variety of mesoderm and neurectoderm-derived tissues, including fibroblasts, endothelial cells, hippocampal and cerebral cortical neurons, and astroglia (Burgess, W. H. and Maciag, T. *Ann. Rev. Biochemistry* 58: 575, 1989). Additional members of the FGF family include: int-2/FGF-3, identified as one of the frequent sites of integration of the mouse mammary tumor virus, and therefore a presumptive oncogenic factor (Smith et al., *EMBO J.* 7: 1013, 1988); FGF-4 (Delli-Bovi et al., *Cell* 50: 729, 1987) and FGF-5 (Zhan et al., *Mol. Cell Biol.* 8, 3487, 1988) as transforming genes in the NIH 3T3 transfection assay; FGF-6, isolated by molecular cloning based on its homology to FGF-4 (Marics et al., *Oncogene* 4: 335 (1989); keratinocyte growth factor/ FGF-7, identified as a mitogen for keratinocytes (Finch et al., *Science* 245: 752, 1989); FGF-8 as an androgen-induced mitogen for mammary carcinoma cells (Tanaka et al., *Proc. Natl. Acad. Sci. USA* 89: 8928, 1992); and FGF-9 as a mitogen for primary astrocytes (Miyamoto et al., *Mol. Cell Biol.* 13: 4251, 1993). Several of the FGFs, including aFGF and bFGF, lack a classical signal sequence; the mechanism by which they are secreted is not known.

All members of the FGF family share approximately 25% or more amino acid sequence identity, a degree of homology indicating that they are likely to share nearly identical three-dimensional structures. Support for this inference comes from a comparison of the three-dimensional structures of bFGF and interleukin 1-beta determined by x-ray diffraction (Eriksson et al., *Proc. Natl. Acad. Sci USA* 88: 3441, 1991; Zhang et al., *Proc. Natl. Acad. Sci USA* 88: 3446, 1991; Ago et al., *J.Biochem.* 110: 360, 1991). Although these proteins share only 10% amino acid identity, the alpha carbon backbones of the two crystal structures can be superimposed with a root-mean square deviation of less than 2 angstroms (Zhang et al., *Proc. Natl. Acad. Sci USA* 88: 3446, 1991). Both proteins consist almost entirely of beta-sheets, which form a barrel composed of three copies of a four-stranded beta-meander motif. The likely heparin- and receptor-binding regions are located on nearby regions on one face of the protein.

aFGF, bFGF, and FGF-7/KGF have been shown to exert some or all of their biological activity through high affinity binding to cell surface tyrosine kinase receptors (e.g., Lee, P. L. et al., *Science* 245: 57, 1989; reviewed in Johnson, D.E. and Williams, L.T., *Adv. Cancer Res.* 60: 1, 1993). Many members of the FGF family also bind tightly to heparin, and a terniary complex of heparin, FGF, and transmembrane receptor may be the biologically relevant signalling species. Thus far four different genes have been identified that encode receptors for FGF family members. Recent work has shown that receptor diversity is increased by differential mRNA splicing within the extracellular ligand binding domain, with the result that multiple receptor isoforms with different ligand binding properties can be encoded by the same gene (Johnson, D. E. and Williams, L. T., *Adv. Cancer Res.* 60: 1, 1993). In tissue culture systems, the binding of aFGF or bFGF to its cell surface receptor activates phospholipase C-gamma (Burgess, W. H. et al., *Mol. Cell Biol.* 10: 4770, 1990), a pathway known to integrate a variety of mitogenic signals.

Identification and characterization of new members of the FGF family will provide insights into the mechanisms by which cells and organs control their growth, survival, senescence, differentiation, and recovery from injury.

SUMMARY OF THE INVENTION

The present invention provides a cell growth, survival and differentiation factor, FHF-2, and a polynucleotide sequence which encodes the factor. This factor is involved in the growth, survival, and or differentiation of cells within the central nervous system (CNS) and in the heart.

The invention provides a method for detecting alterations in FHF-2 gene expression which are diagnostic of neurodegenerative, neoplastic, or cardiac disorders. In another embodiment, the invention provides a method for treating a neurodegenerative, neoplastic or cardiac disorder by enhancing or suppressing the expression or activity of FHF-2.

BRIEF DESCRIPTION OF THE DRAWINGS

FIG. 1 shows the nucleotide and predicted amino acid sequence of human FHF-2 SEQ ID NO:1 and SEQ ID NO:2.

FIG. 2 shows an alignment of the amino acid sequence of human FHF-2 and each of the published nine members of the FGF family. Conserved residues are highlighted. The FGF family members are: aFGF/FGF-1 (SEQ ID NO:22.) (Jaye et al., Science 233: 541, 1986), bFGF/FGF-2 (SEQ ID NO:24.) (Abraham et al., Science 233: 545, 1986), int-2/FGF-3 (SEQ ID NO:17.) (Smith et al., EMBO J. 7: 1013, 1988), FGF-4 (SEQ ID NO:19.) (Delli-Bovi et al., Cell 50: 729, 1987), FGF-5 (SEQ ID NO:18.) (Zhan et al., Mol. Cell Biol. 8, 3487, 1988), FGF-6 (SEQ ID NO:20.) (Marics et al., Oncogene 4: 335, 1989); keratinocyte growth factor/ FGF-7 (SEQ ID NO:23.) (Finch et al., Science 245: 752, 1989), FGF-8 (SEQ ID NO:16.) (Tanaka et al., Proc. Natl. Acad. Sci. USA 89: 8928, 1992), and FGF-9 (SEQ ID NO:21.) (Miyamoto et al., Mol. Cell Biol. 13: 4251, 1993).

DETAILED DESCRIPTION OF THE INVENTION

Figure 3:
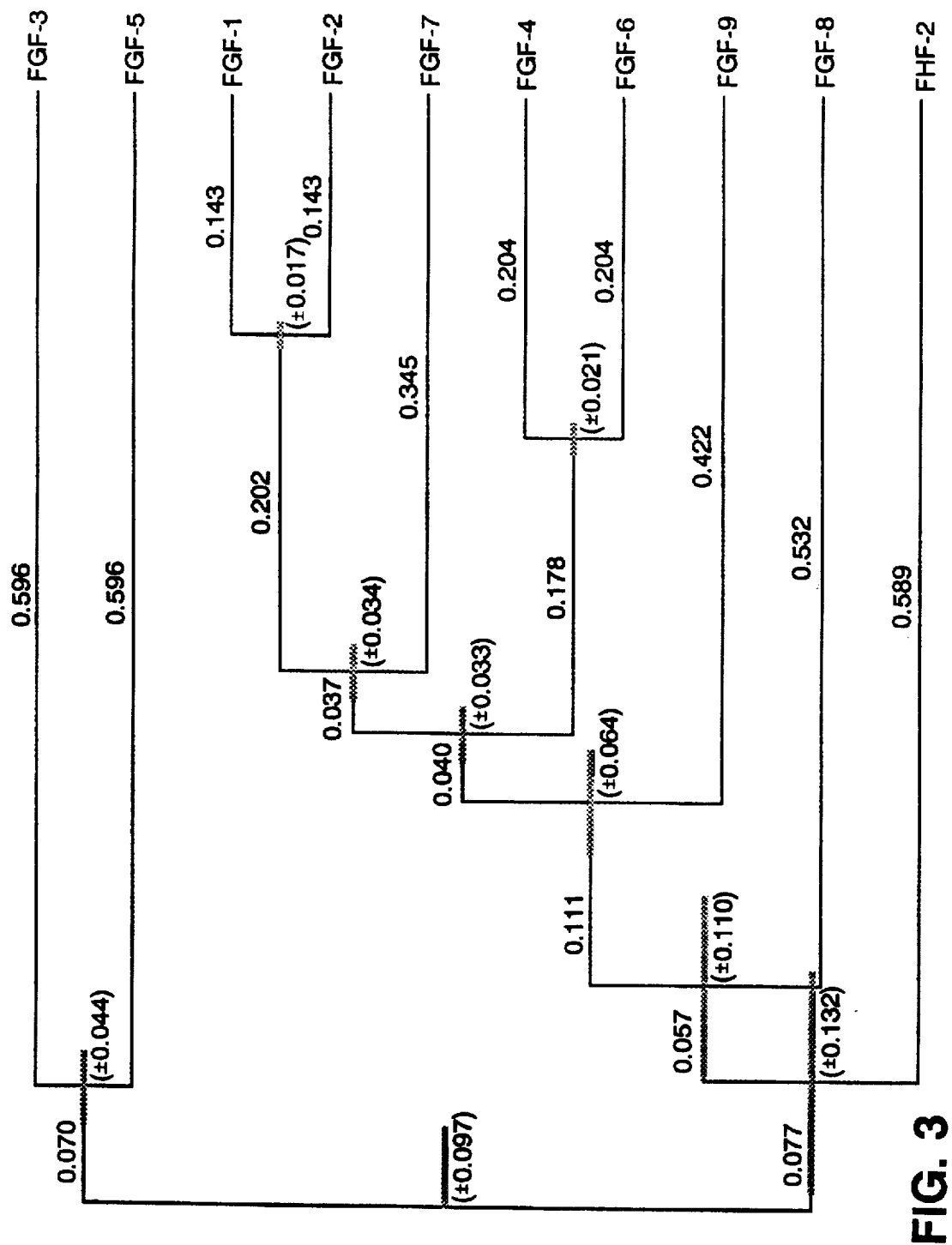
FIG. 3 shows a dendrogram in which the length of each path connecting any pair of FGF family members is proportional to the degree of amino acid sequence divergence of that pair.

The present invention provides a growth factor, FHF-2, and a polynucleotide sequence encoding FHF-2. FHF-2 is expressed at high levels in brain and heart tissues. In one embodiment, the invention provides a method for detection of a cell proliferative or immunologic disorder of central nervous system or cardiac tissue origin which is associated with FHF-2 expression or function. In another embodiment, the invention provides a method for treating a cell proliferative or immunologic disorder by using an agent which suppresses or enhances FHF-2 expression or activity.

The structural homology between the FHF-2 protein of this invention and the members of the FGF family, indicates that FHF-2 is a new member of the family of growth factors. Based on the known activities of many of the other members, it can be expected that FHF-2 will also possess biological activities that will make it useful as a diagnostic and therapeutic reagent.

Many growth factors have expression patterns or possess activities that relate to the function of the nervous system. For example, one growth factor in the TGF family, namely GDNF, has been shown to be a potent neurotrophic factor that can promote the survival of dopaminergic neurons (Lin, el al., *Science*, 260:1130). Another family member, namely dorsalin-1, is capable of promoting the differentiation of neural crest cells (Basler, et al., *Cell*, 73:687, 1993). The inhibins and activins have been shown to be expressed in the brain (Meunier, et al., *Proc. Nat'l. Acad Sci., USA*, 85:247, 1988; Sawchenko, el al., *Nature*, 334:615, 1988), and activin has been shown to be capable of functioning as a nerve cell survival molecule (Schubert, et al., *Nature*, 344:868, 1990). Another TGF family member, namely GDF-1, is nervous system-specific in its expression pattern (Lee, *Proc. Nat'l. Acad. Sci., USA*, 88:4250, 1991), and certain other family members, such as Vgr-1 (Lyons, et al., *Proc. Nat'l. Acad.*

*Sci., USA*, 86:4554, 1989; Jones, et al., *Development*, 111:581, 1991), OP-1 (Ozkaynak, et al., *J. Biol. Chem.*, 267:25220, 1992), and BMP-4 (Jones, et al., *Development*, 111:531, 1991), are also known to be expressed in the nervous system.

The expression of FHF-2 in brain and eye suggests that FHF-2 may also possess activities that relate to the function of the nervous system. The known neurotrophic activities of other members of this family and the expression of FHF-2 in muscle suggest that one activity of FHF-2 may be as a trophic factor for motor neurons. Alternatively, FHF-2 may have neurotrophic activities for other neuronal populations. Hence, FHF-2 may have in vitro and in vivo applications in the treatment of neurodegenerative diseases, such as amyotrophic lateral sclerosis, or in maintaining cells or tissues in culture prior to transplantation.

Growth factors have also been shown to inhibit the differentiation of myoblasts in culture (Massague, et al., *Proc. Natl. Acad. Sci., USA* 83:8206, 1986). Moreover, because myoblast cells may be used as a vehicle for delivering genes to muscle for gene therapy, the properties of FHF-2, namely the elevated expression in heart tissue (i.e., muscle), could be exploited for maintaining cells prior to transplantation or for enhancing the efficiency of the fusion process.

In a first embodiment, the invention provides substantially pure fibroblast growth factor homologous factor-2 (FHF-2) characterized by having a molecular weight of about 30 kD as determined by reducing SDS-PAGE and having essentially the amino acid sequence of SEQ ID NO:2. The term "substantially pure" as used herein refers to FHF-2 which is substantially free of other proteins, lipids, carbohydrates or other materials with which it is naturally associated. One skilled in the art can purify FHF-2 using standard techniques for protein purification. The substantially pure polypeptide will yield a single major band on a non-reducing polyacrylamide gel. The purity of the FHF-2 polypeptide can also be determined by amino-terminal amino acid sequence analysis. FHF-2 polypeptide includes functional fragments of the polypeptide, as long as the activity of FHF-2 remains. Smaller peptides containing the biological activity of FHF-2 are included in the invention.

The invention provides polynucleotides encoding the FHF-2 protein. These polynucleotides include DNA, cDNA and RNA sequences which encode FHF-2. It is understood that all polynucleotides encoding all or a portion of FHF-2 are also included herein, as long as they encode a polypeptide with FHF-2 activity. Such polynucleotides include naturally occurring, synthetic, and intentionally manipulated polynucleotides. For example, FHF-2 polynucleotide may be subjected to site-directed mutagenesis. The polynucleotide sequence for FHF-2 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of FHF-2 polypeptide encoded by the nucleotide sequence is functionally unchanged.

Specifically disclosed herein is a DNA sequence encoding the human FHF-2 gene. The sequence contains an open reading frame encoding a polypeptide 245 amino acids in length. The human FHF-2 inititiator methionine codon shown in FIG. 1 at position 352–354 corresponds to the location of the initiator methionine codon of another FGF family member, FHF-1, when the two sequences are aligned;

a good consensus ribosome binding site (TGGCCATGG; Kozak, *Nucleic Acids Res.*, 15: 8125, 1987) is found at this position. The next methionine codon within the open reading frame is encountered 124 codons 3' of the putative initiator methionine codon. As observed for aFGF and bFGF, the amino-terminus of the primary translation product of FHF-2 does not conform to the consensus sequence for a signal peptide to direct cotranslational insertion across the endoplasmic reticulum membrane. The FHF-2 sequence has one potential asn-X-ser/thr site for asparagine-linked glycosylation four amino acids from the carboxy-terminus. Preferably, the human FHF-2 nucleotide sequence is SEQ ID NO:1 and the deduced amino acid sequence is probably SEQ ID NO:2.

The polynucleotide encoding FHF-2 includes SEQ ID NO:1 as well as nucleic acid sequences complementary to SEQ ID NO:1. A complementary sequence may include an antisense nucleotide. When the sequence is RNA, the deoxynucleotides A, G, C, and T of SEQ ID NO:1 is replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:2 under physiological conditions. Specifically, the fragments should hybridize to DNA encoding FHF-2 protein under stringent conditions.

The most homologous FGF family member is FGF-9, which shares 28% amino acid identity with FHF-2, when aligned with 6 gaps. Minor modifications of the FHF-2 primary amino acid sequence may result in proteins which have substantially equivalent activity as compared to the FHF-2 polypeptide described herein. Such proteins include those as defined by the term "having essentially the amino acid sequence of SEQ ID NO:2". Such modifications may be deliberate, as by site-directed mutagenesis, or may be spontaneous. All of the polypeptides produced by these modifications are included herein as long as the biological activity of FHF-2 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for FHF-2 biological activity.

The nucleotide sequence encoding the FHF-2 polypeptide of the invention includes the disclosed sequence (SEQ ID NO:2), and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the FHF-2 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

The development of specific DNA sequences encoding FHF-2 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for FHF-2peptides having at least one epitope, using antibodies specific for FHF-2. Such antibodies can be either polyclonally or monoclonally derived and used to detect expression product indicative of the presence of FHF-2 cDNA.

DNA sequences encoding FHF-2 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the FHF-2 polynucleotide sequences may be inserted into a recombinant expression vector. The term "recombinant expression vector" refers to a plasmid, virus or other vehicle known in the art that has been manipulated by insertion or incorporation of the FHF-2 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J.Biol Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding FHF-2 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the FHF-2 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The FHF-2 polypeptides of the invention can also be used to produce antibodies which are immunoreactive or bind to epitopes of the FHF-2 polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, el al., ed., 1989).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, N.Y. (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the FHF-2 polypeptide of the invention can be prepared using an intact polypeptide or fragments containing small peptides of interest as the immunizing antigen. The polypeptide or a peptide used to immunize an animal can be derived from translated cDNA (see for example, EXAMPLE 4) or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "cell-proliferative disorder" denotes malignant as well as non-malignant cell populations which often appear to differ from the surrounding tissue both morphologically and genotypically. Malignant cells (i.e. cancer) develop as a result of a multistep process. The FHF-2 polynucleotide that is an antisense molecule is useful in treating malignancies of the various organ systems, particularly, for example, cells in the central nervous system, including neural tissue, heart, and cells of the eye. Essentially, any disorder which is etiologically linked to altered expression of FHF-2 could be considered susceptible to treatment with a FHF-2 suppressing reagent. One such disorder is a malignant cell proliferative disorder, for example.

For purposes of the invention, an antibody or nucleic acid probe specific for FHF-2 may be used to detect FHF-2 polypeptide (using antibody) or polynucleotide (using nucleic acid probe) in biological tissues or fluids. The invention provides a method for detecting a cell proliferative disorder of cardiac tissue or neural tissue, for example, which comprises contacting an anti-FHF-2 antibody or nucleic acid probe with a cell suspected of having a FHF-2 associated disorder and detecting binding of FHF-2 antigen or mRNA to the antibody or nucleic acid probe, respectively. The antibody or nucleic acid probe reactive with FHF-2 is preferably labeled with a compound which allows detection of binding to FHF-2. Any specimen containing a detectable amount of antigen can be used. A preferred sample of this invention is neural tissue or heart tissue. The level of FHF-2 in the suspect cell can be compared with the level in a normal cell to determine whether the subject has a FHF-2-associated cell proliferative disorder. Preferably the subject is human.

When the cell component is nucleic acid, it may be necessary to amplify the nucleic acid prior to binding with an FHF-2 specific probe. Preferably, polymerase chain reaction (PCR) is used, however, other nucleic acid amplification procedures such as ligase chain reaction (LCR), ligated activated transcription (LAT) and nucleic acid sequence-based amplification (NASBA) may be used.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and noncompetitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies or polynucleotides of the invention can be used in vitro and in vivo to monitor the course of amelioration of a FHF-2-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the FHF-2-associated disease is effective. The term "ameliorate" denotes a lessening of the detrimental effect of the FHF-2-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Detection of elevated levels of FHF-2 expression is accomplished by hybridization of nucleic acids isolated from a cell suspected of having an FHF-2 associated proliferative disorder with an FHF-2 polynucleotide of the invention. Analyses, such as Northern Blot analysis, are utilized to quantitate expression of FHF-2. Other standard nucleic acid detection techniques will be known to those of skill in the art.

Treatment of an FHF-2 associated cell proliferative disorder include modulation of FHF-2 gene expression and FHF-2 activity. The term "modulate" envisions the suppression of expression of FHF-2 when it is over-expressed, or augmentation of FHF-2 expression when it is under-expressed. Where a cell-proliferative disorder is associated with the expression of FHF-2, nucleic acid sequences that interfere with FHF-2 expression at the translational level can be used. This approach utilizes, for example, antisense nucleic acid, ribozymes, or triplex agents to block transcription or translation of a specific FHF-2 mRNA, either by masking that mRNA with an antisense nucleic acid or triplex agent, or by cleaving it with a ribozyme. Such disorders include neurodegenerative diseases, for example.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target FHF-2-producing cell. The use of antisense methods to inhibit the in vitro translation of genes is well known in the art (Marcus-Sakura, *Anal. Biochem.*, 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med.Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by FHF-2 protein. Such therapy would achieve its therapeutic effect by introduction of the FHF-2 antisense polynucleotide into cells having the proliferative disorder. Delivery of antisense FHF-2 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a FHF-2 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the FHF-2 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for FHF-2 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of FHF-2 in heart, eye, and brain, or neural tissue, there are a variety of applications using the polypeptide, polynucleotide, and antibodies of the invention, related to these tissues. Such applications include treatment of cell proliferative and immunologic disorders involving these and other tissues. In addition, FHF-2 may be useful in various gene therapy procedures.

The identification of a novel member of the FGF family provides a useful tool for diagnosis, prognosis and therapeutic strategies associated with FHF-2 mediated disorders.

Measurement of FHF-2 levels using anti-FHF-2, antibodies is useful diagnostic for following the progression or recovery from diseases of the nervous system, including: cancer, stroke, neurodegenerative diseases such as Parkinson's disease or Alzheimer's disease, retinal diseases such as retinitis pigmentosa, or viral encephalitis. The presence of high levels of FHF-2 in the central nervous system suggests that the observed low level of FHF-2 in a number of peripheral tissues could reflect FHF-2 in peripheral nerve, and therefore measurement of FHF-2 levels using anti-FHF-2 antibodies could be diagnostic for peripheral neuropathy. The presence of high levels of FHF-2 in the heart suggests that measurement of FHF-2 levels using anti-FHF-2 antibodies is useful as a diagnostic for myocardial infarction, viral endocarditis, or other cardiac disorders.

Like other members of the FGF family, FHF-2 likely has mitogenic and/or cell survival activity, therefore FHF-2 or an analogue that mimics FHF-2 action could be used to promote tissue repair or replacement. The presence of FHF-2 in the CNS suggests such a therapeutic role in diseases of the nervous system, including: stroke, neurodegenerative diseases such as Parkinson's disease or Alzheimer's disease, or in retinal degenerative diseases such as retinitis pigmentosa or macular degeneration, or in peripheral neuropathies. The presence of high levels of FHF-2 in the heart suggests that FHF-2 or an analogue of FHF-2 could be used to accelerate recovery from myocardial infarction or could promote increased cardiac output by increasing heart muscle. Conversely, blocking FHF-2 action either with anti-FHF-2 antibodies or with an FHF-2 antagonist might slow or ameliorate diseases in which excess cell growth is pathological, most obviously cancer.

The following examples are intended to illustrate but not limit the invention. While they are typical of those that might be used, other procedures known to those skilled in the art may alternatively be used.

EXAMPLE 1

Isolation Of FHF-2, A Novel Member Of The FGF Family

To identify novel gene products expressed in the human retina, random segments of human retina cDNA clones were partially sequenced, and the resulting partial sequences compared to the sequences available in the public databases.

In detail, an adult human retina cDNA library constructed in lambda gt10 (Nathans, et al., *Science*, 232: 193, 1986) was amplified, and the cDNA inserts were excised en mass by cleavage with EcoR I and purified free of the vector by agarose gel electrophoresis. Following heat denaturation of the purified cDNA inserts, a synthetic oligonucleotide containing an EcoR I site at its 5' end and six random nucleotides at its 3' end (5' GACGAGATATTAGAATTCT-ACTCGNNNNNN)(SEQ ID NO:3) was used to prime two sequential rounds of DNA synthesis in the presence of the Klenow fragment of *E. coli* DNA polymerase. The resulting duplex molecules were amplified using the polymerase chain reaction (PCR) with a primer corresponding to the unique 5' flanking sequence (5' CCCCCCCCCGACG-AGATATTAGAATTCTACTCG)(SEQ ID NO:4). These PCR products, representing a random sampling of the original cDNA inserts, were cleaved with EcoR I, size fractionated by preparative agarose gel electrophoresis to include only segments of approximately 500 bp in length, and cloned into lambda gt10. Three thousand single plaques from this derivative library were arrayed in 96-well trays and from these clones the inserts were amplified by PCR using flanking vector primers and then sequenced using the dideoxy method and automated fluorescent detection (Applied Biosystems). A single sequencing run from one end of each insert was conceptually translated on both strands in all three reading frames and the six resulting amino acid sequences were used to search for homology in the GenBank nonredundant protein database using the BLASTX searching algorithm.

One partial cDNA sequence was found that showed statistically significant homology to previously described members of the FGF family. Using this partial cDNA as a probe, multiple independent cDNA clones were isolated from the human retina cDNA library, including two that encompass the entire open reading frame and from which complete nucleotide sequences were determined. This sequence was named FHF-1 and is the subject of a pending patent application. (U.S. patent application Ser. No. 08/439, 725, "Fibroblast Growth Factor Homologous Factor-1 (FHF-1) and Methods of Use," Nathans et al., filed May 12, 1995). A search of partial cDNA sequences ('expressed sequence tags', ESTs) in the public databases revealed a human adult test is cDNA fragment (NCBI ID 28057, EST ID EST06895, Genbank ID T09003; Adams, et al., *Nature Genetics*, 4: 373, 1993) with strong homology to FHF-1, but only weak homology to other members of the FGF family. The homology between this EST and other members of the FGF family is sufficiently low that no indication of that homology was noted in the description associated with the clone in Genbank or in the publication describing the EST sequence (Adams, et al.,supra, 1993). Based on the EST sequence, this fragment was amplified by PCR from a human retina cDNA library and used as a probe to isolate multiple independent cDNA clones from that library, including two that encompass the entire open reading frame and from which complete nucleotide sequences were determined. This sequence was named FHF-2.

EXAMPLE 2

Deduced Primary Structure Of FHF-2

FIG. 1 shows the sequence of human FHF-2 deduced from the nucleotide sequences of two independent human retina cDNA clones. The primary translation product of human FHF-2 is predicted to be 245 amino acids in length. The human FHF-2 inititiator methionine codon shown in FIG. 1 at position 352–354 corresponds to the location of the initiator methionine codon of FHF-1 when the two sequences are aligned; a good consensus ribosome binding site (TGGCCATGG; Kozak, *Nucleic Acids Res.*, 15: 8125, 1987)(SEQ ID NO:5) is found at this position. The next methionine codon within the open reading frame is encountered 124 codons 3' of the putative initiator methionine codon. As observed for aFGF and bFGF, the amino-terminus of the primary translation product of FHF-2 does not conform to the consensus sequence for a signal peptide to direct cotranslational insertion across the endoplasmic reticulum membrane. The FHF-2 sequence has one potential asn-X-ser/thr site for asparagine-linked glycosylation four amino acids from the carboxy-terminus.

Alignment of FHF-2 with the other known members of the FGF family is shown in FIG. 2 and a dendrogram showing the degree of amino acid similarity is shown in FIG. 3 The most homologous FGF family member is FGF-9 which shows 28% amino acid identity with FHF-2 when aligned with 6 gaps. Note that in the central region of each polypeptide, all FGF family members, including FHF-2, share 11 invariant amino acids.

EXAMPLE 3

Chromosomal Localization Of FHF-2

Figure 4:
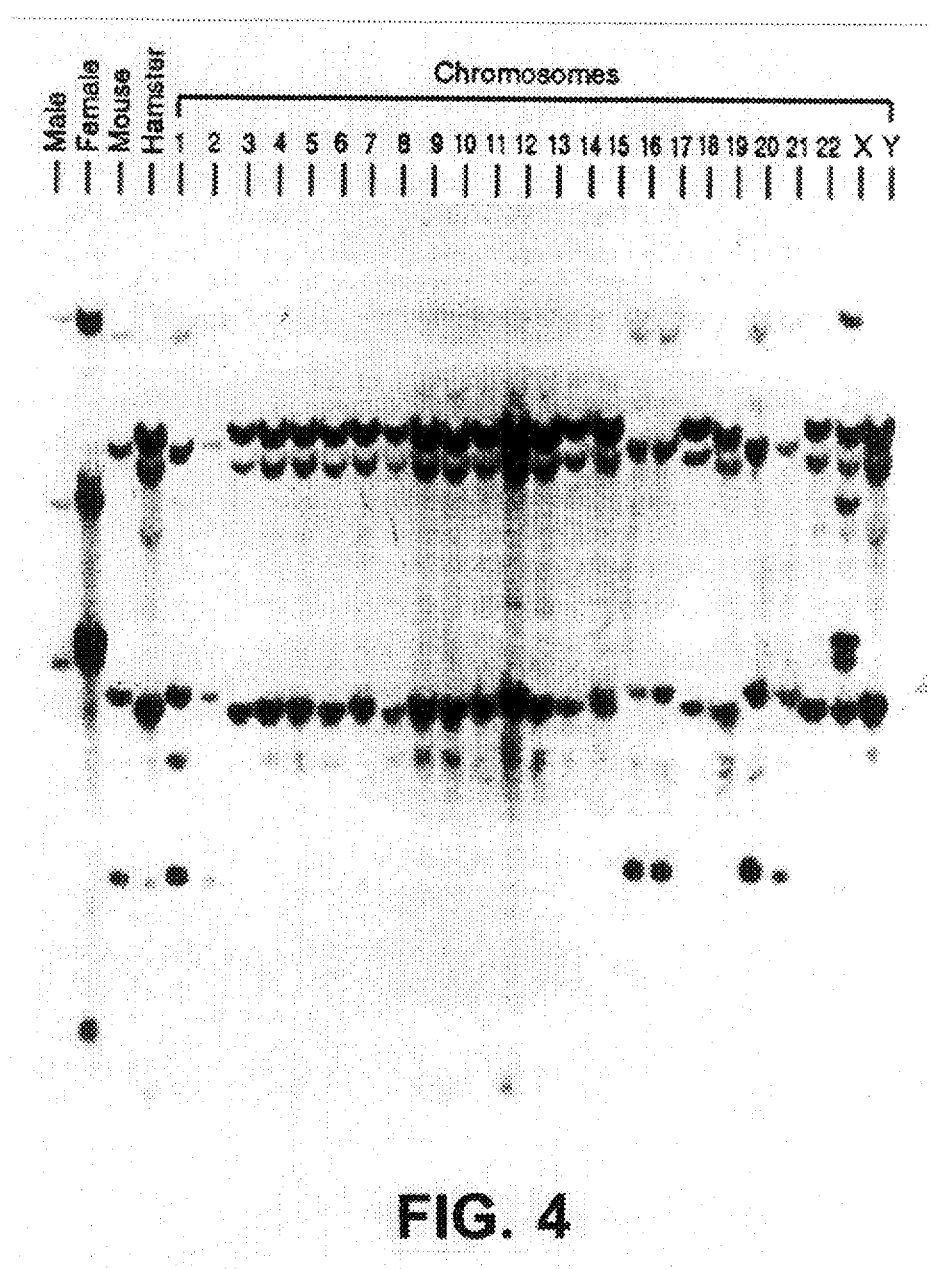
FIG. 4 shows the location of the gene encoding FHF-2 on the human X-chromosome. A Southern blot was prepared from DNA derived from mouse-human or hamster-human hybrid cell lines, each of which contains a single human chromosome, indicated above each lane. The human specific hybridization is found on the X-chromosome.

The chromosomal location of FHF-2 was determined by probing a Southern blot containing restriction enzyme digested DNA derived from a panel of 24 human-mouse and human-hamster cell lines, each containing a different human chromosome (Oncor, Gaithersburg, Md.). As seen in FIG. 4, hybridization of the human FHF-2 probe to human, mouse, and hamster genomic DNA produces distinct hybridizing fragment sizes. The human-specific hybridization pattern is seen only in the lane corresponding to the hybrid cell line carrying the human X-chromosome.

EXAMPLE 4

Production Of FHF-2 In Transfected Human Cells

Figure 5:
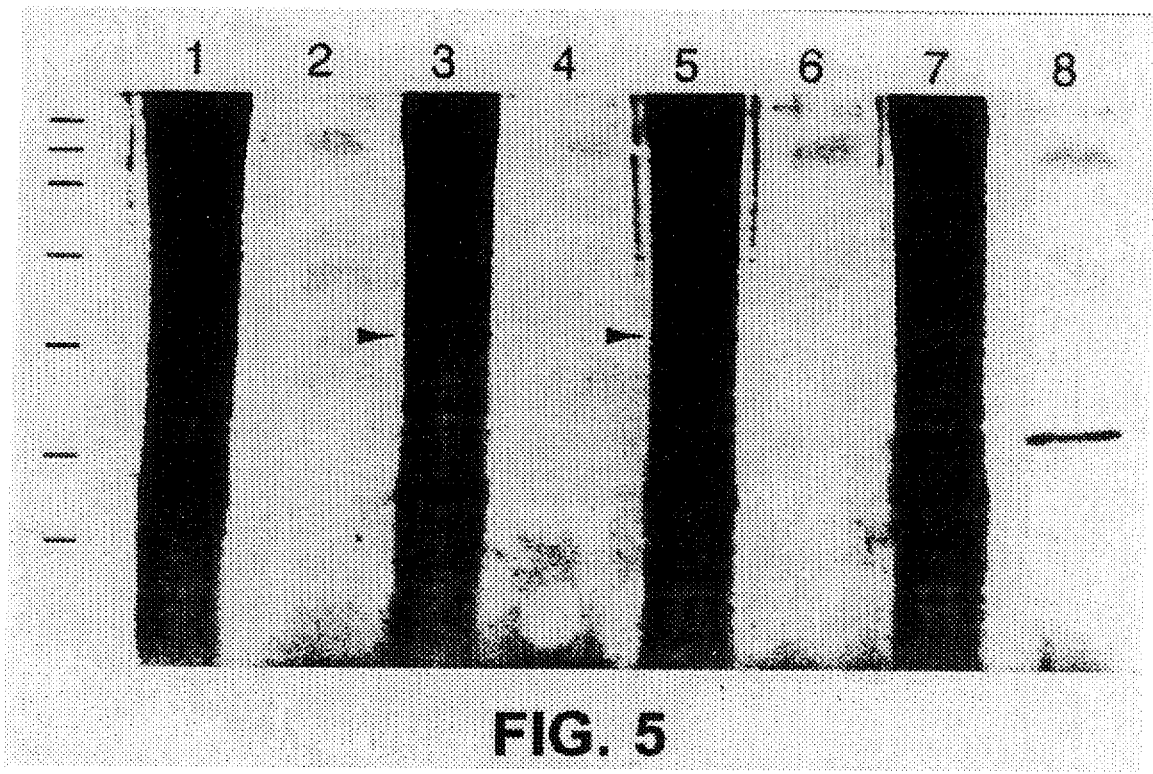
FIG. 5 shows the production of FHF-2 in transfected human embryonic kidney cells. Proteins were labeled biosynthetically with $^{35}$S-methionine and resolved by SDS-polyacrylamide gel electrophoresis. Lanes 1, 3, 5, and 7: total cell protein; lanes 2, 4, 6, and 8: protein present in the medium (secreted protein). Lanes 1 and 2, mock transfected cells; lanes 3 and 4, transfection with cDNA encoding FHF-1, a closely related member of the FGF family; lanes 5 and 6, transfection with cDNA encoding FHF-2; lanes 7 and 8, transfection with cDNA encoding human growth hormone. Arrows indicate the FHF-1 and FHF-2 protein bands. Protein standards are shown to the left; from top to bottom their molecular masses are 220, 97, 66, 46, 30, 21.5, and 14.3 kD.

To express FHF-2 in human cells, the complete open reading frame was inserted into the eukaryotic expression vector pCIS (Gorman, et al., *DNA Protein Eng. Tech.*, 2: 3, 1990). To increase the efficiency of translation, the region immediately 5' of the initiator methionine coding was converted to an optimal ribosome binding site (CCACCATGG) (SEQ ID NO:5) by cutting the FHF-2 coding region at the initiator methionine with Nco I (which recognizes CCATGG) and ligating to the expression vector. Following transient transfection of human embryonic kidney cells with the expression construct and a plasmid expressing the simian virus 40 (SV40) large T-antigen (pRSV-TAg; Gorman et al.,supra), cells were metabolically labeled with $^{35}$S methionine for 6 hours in the absence of serum. As shown in FIG. 5, cells transfected with FHF-2 synthesize a single polypeptide with an apparent molecular mass of 30 kD that is not produced by untransfected cells or by cells transfected with an unrelated construct. This polypeptide corresponds closely to the predicted molecular mass of the primary translation product, 27.6 kD. FIG. 5 also shows that cells transfected with a human growth hormone (hGH) expression plasmid efficiently secrete hGH, whereas FHF-2 accumulates within the transfected cells and fails to be secreted in detectable quantities.

EXAMPLE 5

Tissue Distribution Of FHF-2 mRNA

Figure 6:
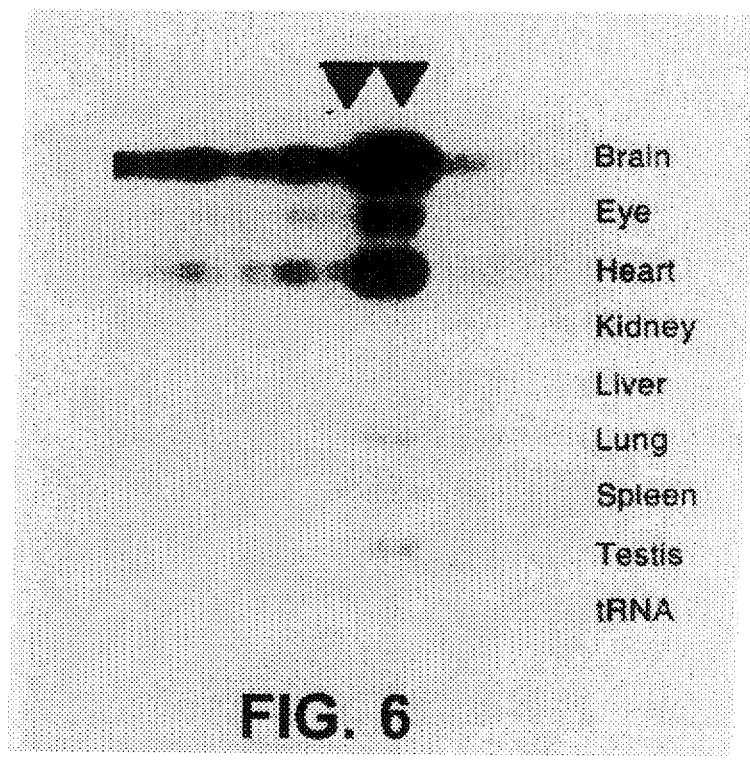
FIG. 6 shows the tissue specificity of FHF-2 expression. Ten micrograms of total RNA from the indicated mouse tissues was prepared (Chomczinski & Sacchi. Anal. Biochem. 162: 156, 1987) and used for RNAse protection (Ausabel et al., Current Protocols in Molecular Biology; New York: Wiley Interscience, 1987) with a mouse FHF-2 antisense probe that spanned 197 bases of the most 3' coding region exon and the adjacent upstream 335 bases of intron sequence. RNAse protection at the size expected for the 197 base exon region of the probe (arrowheads) was observed with RNA from brain, eye, and heart. A longer exposure reveals barely visible bands in all of the other tissues but not in the tRNA control sample.

To determine the tissue distribution of FHF-2 mRNA, RNase protection analysis was performed on total RNA from mouse brain, eye, heart, kidney, liver, lung, spleen, and testis, as well as a yeast tRNA negative control. The probe used was derived from a segment of the mouse FHF-2 gene isolated by hybridization with the full-length human FHF-2 cDNA. As seen in FIG. 6, the highest levels of FHF-2 expression are in the brain, eye, and heart. Very low levels of FHF-2 expression were detected in all of the other tisssues on a longer exposure of the autoradiogram.

Although the invention has been described with reference to the presently preferred embodiment, it should be understood that various modifications can be made without departing from the spirit of the invention. Accordingly, the invention is limited only by the following claims.

---

We claim:

1. An isolated polynucleotide sequence encoding the fibroblast growth factor homologous factor-2 (FHF-2) polypeptide having the amino acid sequence of SEQ ID NO:2.

2. An isolated polynucleotide selected from the group consisting of:
   a) SEQ ID NO:1;
   b) SEQ ID NO:1, wherein T can also be U; and
   c) the nucleic acid sequence complementary to SEQ ID NO:1.

3. The polynucleotide sequence of claim 1, wherein the polynucleotide is isolated from a mammalian cell.

4. The polynucleotide of claim 3, wherein the mammalian cell is a human cell.

5. An expression vector comprising the polynucleotide of claim 1.

6. The vector of claim 5, wherein the vector is a plasmid.

7. The vector of claim 5, wherein the vector is a virus.

8. A host cell stably transformed with the vector of claim 5.

9. The host cell of claim 8, wherein the cell is prokaryotic.

10. The host cell of claim 8, wherein the cell is eukaryotic.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
    ( A ) LENGTH: 1150 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 353..1087

( x i ) SEQUENCE DESCRIPTION: SEQ ID NO:1:

```
AATTCCGCTT  GCACAGTGTC  CGCCGGGCGC  AGGGGCCGAC  CGCACGCAGT  CGCGCAGTTC      60

TGCCTCCGCC  TGCCAGTCTC  GCCCGCGATC  CCGGCCCGGG  GCTGTGGCGT  CGACTCCGAC     120

CCAGGCAGCC  AGCAGCCCGC  GCGGGAGCCG  GACCGCCGCC  GGAGGAGCTC  GGACGGCATG     180

CTGAGCCCCC  TCCTTGGCTG  AAGCCCGAGT  GCGGAGAAGC  CCGGGCAAAC  GCAGGCTAAG     240

GAGACCAAAG  CGGCGAAGTC  GCGAGACAGC  GGACAAGCAG  CGGAGGAGAA  GGAGGAGGAG     300

GCGAACCCAG  AGAGGGGCAG  CAAAAGAAGC  GGTGGTGGTG  GGCGTCGTGG  CC  ATG         355
                                                                Met
                                                                  1

GCG  GCG  GCT  ATC  GCC  AGC  TCG  CTC  ATC  CGT  CAG  AAG  AGG  CAA  GCC  CGC   403
Ala  Ala  Ala  Ile  Ala  Ser  Ser  Leu  Ile  Arg  Gln  Lys  Arg  Gln  Ala  Arg
               5                        10                        15

GAG  CGC  GAG  AAA  TCC  AAC  GCC  TGC  AAG  TGT  GTC  AGC  AGC  CCC  AGC  AAA   451
Glu  Arg  Glu  Lys  Ser  Asn  Ala  Cys  Lys  Cys  Val  Ser  Ser  Pro  Ser  Lys
              20                        25                        30

GGC  AAG  ACC  AGC  TGC  GAC  AAA  AAC  AAG  TTA  AAT  GTC  TTT  TCC  CGG  GTC   499
Gly  Lys  Thr  Ser  Cys  Asp  Lys  Asn  Lys  Leu  Asn  Val  Phe  Ser  Arg  Val
         35                        40                        45

AAA  CTC  TTC  GGC  TCC  AAG  AAG  AGG  CGC  AGA  AGA  AGA  CCA  GAG  CCT  CAG   547
Lys  Leu  Phe  Gly  Ser  Lys  Lys  Arg  Arg  Arg  Arg  Arg  Pro  Glu  Pro  Gln
50                        55                        60                        65

CTT  AAG  GGT  ATA  GTT  ACC  AAG  CTA  TAC  AGC  CGA  CAA  GGC  TAC  CAC  TTG   595
Leu  Lys  Gly  Ile  Val  Thr  Lys  Leu  Tyr  Ser  Arg  Gln  Gly  Tyr  His  Leu
                    70                        75                        80
```

-continued

| | | | | | | | | | | | | | | | | |
|---|---|---|---|---|---|---|---|---|---|---|---|---|---|---|---|---|
| CAG | CTG | CAG | GCG | GAT | GGA | ACC | ATT | GAT | GGC | ACC | AAA | GAT | GAG | GAC | AGC | 643 |
| Gln | Leu | Gln | Ala | Asp | Gly | Thr | Ile | Asp | Gly | Thr | Lys | Asp | Glu | Asp | Ser | |
| | | | 85 | | | | | 90 | | | | | 95 | | | |
| ACT | TAC | ACT | CTG | TTT | AAC | CTC | ATC | CCT | GTG | GGT | CTG | CGA | GTG | GTG | GCT | 691 |
| Thr | Tyr | Thr | Leu | Phe | Asn | Leu | Ile | Pro | Val | Gly | Leu | Arg | Val | Val | Ala | |
| | | 100 | | | | | 105 | | | | | 110 | | | | |
| ATC | CAA | GGA | GTT | CAA | ACC | AAG | CTG | TAC | TTG | GCA | ATG | AAC | AGT | GAG | GGA | 739 |
| Ile | Gln | Gly | Val | Gln | Thr | Lys | Leu | Tyr | Leu | Ala | Met | Asn | Ser | Glu | Gly | |
| | 115 | | | | | 120 | | | | | 125 | | | | | |
| TAC | TTG | TAC | ACC | TCG | GAA | CTT | TTC | ACA | CCT | GAG | TGC | AAA | TTC | AAA | GAA | 787 |
| Tyr | Leu | Tyr | Thr | Ser | Glu | Leu | Phe | Thr | Pro | Glu | Cys | Lys | Phe | Lys | Glu | |
| 130 | | | | | 135 | | | | | 140 | | | | | 145 | |
| TCA | GTG | TTT | GAA | AAT | TAT | TAT | GTG | ACA | TAT | TCA | TCA | ATG | ATA | TAC | CGT | 835 |
| Ser | Val | Phe | Glu | Asn | Tyr | Tyr | Val | Thr | Tyr | Ser | Ser | Met | Ile | Tyr | Arg | |
| | | | | 150 | | | | | 155 | | | | | 160 | | |
| CAG | CAG | CAG | TCA | GGC | CGA | GGG | TGG | TAT | CTG | GGT | CTG | AAC | AAA | GAA | GGA | 883 |
| Gln | Gln | Gln | Ser | Gly | Arg | Gly | Trp | Tyr | Leu | Gly | Leu | Asn | Lys | Glu | Gly | |
| | | | 165 | | | | | 170 | | | | | 175 | | | |
| GAG | ATC | ATG | AAA | GGC | AAC | CAT | GTG | AAG | AAG | AAC | AAG | CCT | GCA | GCT | CAT | 931 |
| Glu | Ile | Met | Lys | Gly | Asn | His | Val | Lys | Lys | Asn | Lys | Pro | Ala | Ala | His | |
| | | 180 | | | | | 185 | | | | | 190 | | | | |
| TTT | CTG | CCT | AAA | CCA | CTG | AAA | GTG | GCC | ATG | TAC | AAG | GAG | CCA | TCA | CTG | 979 |
| Phe | Leu | Pro | Lys | Pro | Leu | Lys | Val | Ala | Met | Tyr | Lys | Glu | Pro | Ser | Leu | |
| | 195 | | | | | 200 | | | | | 205 | | | | | |
| CAC | GAT | CTC | ACG | GAG | TTC | TCC | CGA | TCT | GGA | AGC | GGG | ACC | CCA | ACC | AAG | 1027 |
| His | Asp | Leu | Thr | Glu | Phe | Ser | Arg | Ser | Gly | Ser | Gly | Thr | Pro | Thr | Lys | |
| 210 | | | | | 215 | | | | | 220 | | | | | 225 | |
| AGC | AGA | AGT | GTC | TCT | GGC | GTG | CTG | AAC | GGA | GGC | AAA | TCC | ATG | AGC | CAC | 1075 |
| Ser | Arg | Ser | Val | Ser | Gly | Val | Leu | Asn | Gly | Gly | Lys | Ser | Met | Ser | His | |
| | | | | 230 | | | | | 235 | | | | | 240 | | |
| AAT | GAA | TCA | ACG | TAGCCAGTGA | GGGCAAAAGA | AGGGCTCTGT | AACAGAACCT | | | | | | | | | 1127 |
| Asn | Glu | Ser | Thr | | | | | | | | | | | | | |
| | | | 245 | | | | | | | | | | | | | |
| TACCTCCAGG | TGCTGTTGAA | TTC | | | | | | | | | | | | | | 1150 |

( 2 ) INFORMATION FOR SEQ ID NO:2:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Ala | Ala | Ile | Ala | Ser | Ser | Leu | Ile | Arg | Gln | Lys | Arg | Gln | Ala |
| 1 | | | | 5 | | | | | 10 | | | | | 15 | |
| Arg | Glu | Arg | Glu | Lys | Ser | Asn | Ala | Cys | Lys | Cys | Val | Ser | Ser | Pro | Ser |
| | | | 20 | | | | | 25 | | | | | 30 | | |
| Lys | Gly | Lys | Thr | Ser | Cys | Asp | Lys | Asn | Lys | Leu | Asn | Val | Phe | Ser | Arg |
| | | 35 | | | | | 40 | | | | | 45 | | | |
| Val | Lys | Leu | Phe | Gly | Ser | Lys | Lys | Arg | Arg | Arg | Arg | Pro | Glu | Pro |
| | 50 | | | | | 55 | | | | | 60 | | | | |
| Gln | Leu | Lys | Gly | Ile | Val | Thr | Lys | Leu | Tyr | Ser | Arg | Gln | Gly | Tyr | His |
| 65 | | | | | 70 | | | | | 75 | | | | | 80 |
| Leu | Gln | Leu | Gln | Ala | Asp | Gly | Thr | Ile | Asp | Gly | Thr | Lys | Asp | Glu | Asp |
| | | | | 85 | | | | | 90 | | | | | 95 | |
| Ser | Thr | Tyr | Thr | Leu | Phe | Asn | Leu | Ile | Pro | Val | Gly | Leu | Arg | Val | Val |
| | | | 100 | | | | | 105 | | | | | 110 | | |

| | | | | | | | | | | | | | | | |
|---|---|---|---|---|---|---|---|---|---|---|---|---|---|---|---|
| Ala | Ile | Gln<br>115 | Gly | Val | Gln | Thr | Lys<br>120 | Leu | Tyr | Leu | Ala | Met<br>125 | Asn | Ser | Glu |
| Gly | Tyr<br>130 | Leu | Tyr | Thr | Ser | Glu<br>135 | Leu | Phe | Thr | Pro | Glu<br>140 | Cys | Lys | Phe | Lys |
| Glu<br>145 | Ser | Val | Phe | Glu | Asn<br>150 | Tyr | Tyr | Val | Thr | Tyr<br>155 | Ser | Ser | Met | Ile | Tyr<br>160 |
| Arg | Gln | Gln | Gln | Ser<br>165 | Gly | Arg | Gly | Trp | Tyr<br>170 | Leu | Gly | Leu | Asn | Lys<br>175 | Glu |
| Gly | Glu | Ile | Met<br>180 | Lys | Gly | Asn | His | Val<br>185 | Lys | Lys | Asn | Lys | Pro<br>190 | Ala | Ala |
| His | Phe | Leu<br>195 | Pro | Lys | Pro | Leu | Lys<br>200 | Val | Ala | Met | Tyr | Lys<br>205 | Glu | Pro | Ser |
| Leu | His<br>210 | Asp | Leu | Thr | Glu | Phe<br>215 | Ser | Arg | Ser | Gly | Ser<br>220 | Gly | Thr | Pro | Thr |
| Lys<br>225 | Ser | Arg | Ser | Val | Ser<br>230 | Gly | Val | Leu | Asn | Gly<br>235 | Gly | Lys | Ser | Met | Ser<br>240 |
| His | Asn | Glu | Ser | Thr<br>245 | | | | | | | | | | | |

( 2 ) INFORMATION FOR SEQ ID NO:3:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

GACGAGATAT TAGAATTCTA CTCGNNNNNN           30

( 2 ) INFORMATION FOR SEQ ID NO:4:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:4:

CCCCCCCCG ACGAGATATT AGAATTCTAC TCG           33

( 2 ) INFORMATION FOR SEQ ID NO:5:

( i ) SEQUENCE CHARACTERISTICS:
      ( A ) LENGTH: 9 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

TGGCCATGG           9

( 2 ) INFORMATION FOR SEQ ID NO:6:

( i ) SEQUENCE CHARACTERISTICS:
      ( A ) LENGTH: 215 amino acids
      ( B ) TYPE: amino acid
      ( C ) STRANDEDNESS: Not Relevant
      ( D ) TOPOLOGY: linear (ii) MOLECULE TYPE: protein (xi) SEQUENCE DESCRIPTION: SEQ ID NO:6:

```
Met Gly Ser Pro Arg Ser Ala Leu Ser Cys Leu Leu Leu His Leu Leu
1               5                   10                  15
Val Leu Cys Leu Gln Ala Gln Val Thr Val Gln Ser Ser Pro Asn Phe
            20                  25                  30
Thr Gln His Val Arg Glu Gln Ser Leu Val Thr Asp Gln Leu Ser Arg
        35                  40                  45
Arg Leu Ile Arg Thr Tyr Gln Leu Tyr Ser Arg Thr Ser Gly Lys His
    50                  55                  60
Val Gln Val Leu Ala Asn Lys Arg Ile Asn Ala Met Ala Glu Asp Gly
65                  70                  75                  80
Asp Pro Phe Ala Lys Leu Ile Val Glu Thr Asp Thr Phe Gly Ser Arg
                85                  90                  95
Val Arg Val Arg Gly Ala Glu Thr Gly Leu Tyr Ile Cys Met Asn Lys
            100                 105                 110
Lys Gly Lys Leu Ile Ala Lys Ser Asn Gly Lys Gly Lys Asp Cys Val
        115                 120                 125
Phe Ile Glu Ile Val Leu Glu Asn Asn Tyr Thr Ala Leu Gln Asn Ala
    130                 135                 140
Lys Tyr Glu Gly Trp Tyr Met Ala Phe Thr Arg Lys Gly Arg Pro Arg
145                 150                 155                 160
Lys Gly Ser Lys Thr Arg Gln His Gln Arg Glu Val His Phe Met Lys
                165                 170                 175
Arg Leu Pro Arg Gly His His Thr Thr Glu Gln Ser Leu Arg Phe Glu
            180                 185                 190
Phe Leu Asn Tyr Pro Pro Phe Thr Arg Ser Leu Arg Gly Ser Gln Arg
        195                 200                 205
Thr Trp Ala Pro Glu Pro Arg
    210                 215
```

(2) INFORMATION FOR SEQ ID NO:7:

(i) SEQUENCE CHARACTERISTICS:
 (A) LENGTH: 245 amino acids
 (B) TYPE: amino acid
 (C) STRANDEDNESS: Not Relevant
 (D) TOPOLOGY: linear (ii) MOLECULE TYPE: protein (xi) SEQUENCE DESCRIPTION: SEQ ID NO:7:

```
Met Gly Leu Ile Trp Leu Leu Leu Leu Ser Leu Leu Glu Pro Ser Trp
1               5                   10                  15
Pro Thr Thr Gly Pro Gly Thr Arg Leu Arg Arg Asp Ala Gly Gly Arg
            20                  25                  30
Gly Gly Val Tyr Glu His Leu Gly Gly Ala Pro Arg Arg Arg Lys Leu
        35                  40                  45
Tyr Cys Ala Thr Lys Tyr His Leu Gln Leu His Pro Ser Gly Arg Val
    50                  55                  60
Asn Gly Ser Leu Glu Asn Ser Ala Tyr Ser Ile Leu Glu Ile Thr Ala
65                  70                  75                  80
Val Glu Val Gly Val Val Ala Ile Lys Gly Leu Phe Ser Gly Arg Tyr
                85                  90                  95
Leu Ala Met Asn Lys Arg Gly Arg Leu Tyr Ala Ser Asp His Tyr Asn
            100                 105                 110
```

| | | | | | | | | | | | | | | |
|---|---|---|---|---|---|---|---|---|---|---|---|---|---|---|
|Ala|Glu|Cys<br>115|Glu|Phe|Val|Glu|Arg<br>120|Ile|His|Glu|Leu|Gly<br>125|Tyr|Asn|Thr|
|Tyr|Ala<br>130|Ser|Arg|Leu|Tyr|Arg<br>135|Thr|Gly|Ser|Ser|Gly<br>140|Pro|Gly|Ala|Gln|
|Arg<br>145|Gln|Pro|Gly|Ala|Gln<br>150|Arg|Pro|Trp|Tyr|Val<br>155|Ser|Val|Asn|Gly|Lys<br>160|
|Gly|Arg|Pro|Arg|Arg<br>165|Gly|Phe|Lys|Thr|Arg<br>170|Arg|Thr|Gln|Lys|Ser<br>175|Ser|
|Leu|Phe|Leu|Pro<br>180|Arg|Val|Leu|Gly|His<br>185|Lys|Asp|His|Glu|Met<br>190|Val|Arg|
|Leu|Leu|Gln<br>195|Ser|Ser|Gln|Pro|Arg<br>200|Ala|Pro|Gly|Glu|Gly<br>205|Ser|Gln|Pro|
|Arg|Gln<br>210|Arg|Arg|Gln|Lys|Lys<br>215|Gln|Ser|Pro|Gly|Asp<br>220|His|Gly|Lys|Met|
|Glu<br>225|Thr|Leu|Ser|Thr|Arg<br>230|Ala|Thr|Pro|Ser|Thr<br>235|Gln|Leu|His|Thr|Gly<br>240|
|Gly|Leu|Ala|Val|Ala<br>245| | | | | | | | | | | |

( 2 ) INFORMATION FOR SEQ ID NO:8:

( i ) SEQUENCE CHARACTERISTICS:
        ( A ) LENGTH: 268 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
|Met<br>1|Ser|Leu|Ser|Phe<br>5|Leu|Leu|Leu|Leu|Phe<br>10|Phe|Ser|His|Leu|Ile<br>15|Leu|
|Ser|Ala|Trp|Ala<br>20|His|Gly|Glu|Lys|Arg<br>25|Leu|Ala|Pro|Lys|Gly<br>30|Gln|Pro|
|Gly|Pro|Ala<br>35|Ala|Thr|Asp|Arg|Asn<br>40|Pro|Ile|Gly|Ser|Ser<br>45|Ser|Arg|Gln|
|Ser|Ser<br>50|Ser|Ser|Ala|Met|Ser<br>55|Ser|Ser|Ser|Ala|Ser<br>60|Ser|Ser|Pro|Ala|
|Ala<br>65|Ser|Leu|Gly|Ser|Gln<br>70|Gly|Ser|Gly|Leu|Glu<br>75|Gln|Ser|Ser|Phe|Gln<br>80|
|Trp|Ser|Pro|Ser|Gly<br>85|Arg|Arg|Thr|Gly|Ser<br>90|Leu|Tyr|Cys|Arg|Val<br>95|Gly|
|Ile|Gly|Phe|His<br>100|Leu|Gln|Ile|Tyr|Pro<br>105|Asp|Gly|Lys|Val|Asn<br>110|Gly|Ser|
|His|Glu|Ala|Asn<br>115|Met|Leu|Ser|Val|Leu<br>120|Glu|Ile|Phe|Ala|Val<br>125|Ser|Gln|
|Gly|Ile<br>130|Val|Gly|Ile|Arg|Gly<br>135|Val|Phe|Ser|Asn|Lys<br>140|Phe|Leu|Ala|Met|
|Ser<br>145|Lys|Lys|Gly|Lys|Leu<br>150|His|Ala|Ser|Ala|Lys<br>155|Phe|Thr|Asp|Asp|Cys<br>160|
|Lys|Phe|Arg|Glu|Arg<br>165|Phe|Gln|Glu|Asn|Ser<br>170|Tyr|Asn|Thr|Tyr|Ala<br>175|Ser|
|Ala|Ile|His|Arg<br>180|Thr|Glu|Lys|Thr|Gly<br>185|Arg|Glu|Trp|Tyr|Val<br>190|Ala|Leu|
|Asn|Lys|Arg<br>195|Gly|Lys|Ala|Lys|Arg<br>200|Gly|Cys|Ser|Pro|Arg<br>205|Val|Lys|Pro|

```
            Gln  His  Ile  Ser  Thr  His  Phe  Leu  Pro  Arg  Phe  Lys  Gln  Ser  Glu  Gln
                 210            215                      220

Pro  Glu  Leu  Ser  Phe  Thr  Val  Thr  Val  Pro  Glu  Lys  Lys  Asn  Pro  Pro
            225                      230                      235                      240

Ser  Pro  Ile  Lys  Ser  Lys  Ile  Pro  Leu  Ser  Ala  Pro  Arg  Lys  Asn  Thr
                                245                      250                      255

Asn  Ser  Val  Lys  Tyr  Arg  Leu  Lys  Phe  Arg  Phe  Gly
                           260                      265
```

( 2 ) INFORMATION FOR SEQ ID NO:9:

( i ) SEQUENCE CHARACTERISTICS:
        ( A ) LENGTH: 206 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:9:

```
            Met  Ser  Gly  Pro  Gly  Thr  Ala  Ala  Val  Ala  Leu  Leu  Pro  Ala  Val  Leu
            1                   5                   10                      15

Leu  Ala  Leu  Leu  Ala  Pro  Trp  Ala  Gly  Arg  Gly  Gly  Ala  Ala  Ala  Pro
                           20                      25                      30

Thr  Ala  Pro  Asn  Gly  Thr  Leu  Glu  Ala  Glu  Leu  Glu  Arg  Arg  Trp  Glu
                      35                      40                      45

Ser  Leu  Val  Ala  Leu  Ser  Leu  Ala  Arg  Leu  Pro  Val  Ala  Ala  Gln  Pro
                 50                      55                      60

Lys  Glu  Ala  Ala  Val  Gln  Ser  Gly  Ala  Gly  Asp  Tyr  Leu  Leu  Gly  Ile
            65                       70                      75                       80

Lys  Arg  Leu  Arg  Arg  Leu  Tyr  Cys  Asn  Val  Gly  Ile  Gly  Phe  His  Leu
                                85                      90                      95

Gln  Ala  Leu  Pro  Asp  Gly  Arg  Ile  Gly  Gly  Ala  His  Ala  Asp  Thr  Arg
                           100                     105                     110

Asp  Ser  Leu  Leu  Glu  Leu  Ser  Pro  Val  Glu  Arg  Gly  Val  Val  Ser  Ile
                      115                     120                     125

Phe  Gly  Val  Ala  Ser  Arg  Phe  Phe  Val  Ala  Met  Ser  Ser  Lys  Gly  Lys
                 130                     135                     140

Leu  Tyr  Gly  Ser  Pro  Phe  Phe  Thr  Asp  Glu  Cys  Ile  Phe  Lys  Glu  Ile
            145                     150                     155                     160

Leu  Leu  Pro  Asn  Asn  Tyr  Asn  Ala  Tyr  Glu  Ser  Tyr  Lys  Tyr  Pro  Gly
                                165                     170                     175

Met  Phe  Ile  Ala  Leu  Ser  Lys  Asn  Gly  Lys  Thr  Lys  Lys  Gly  Asn  Arg
                           180                     185                     190

Val  Ser  Pro  Thr  Met  Lys  Val  Thr  His  Phe  Leu  Pro  Arg  Leu
                      195                     200                     205
```

( 2 ) INFORMATION FOR SEQ ID NO:10:

( i ) SEQUENCE CHARACTERISTICS:
        ( A ) LENGTH: 198 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:10:

```
            Met  Ser  Arg  Gly  Ala  Gly  Arg  Leu  Gln  Gly  Thr  Leu  Trp  Ala  Leu  Val
            1                   5                   10                      15
```

```
Phe  Leu  Gly  Ile  Leu  Val  Gly  Met  Val  Val  Pro  Ser  Pro  Ala  Gly  Thr
               20                  25                  30

Arg  Ala  Asn  Asn  Thr  Leu  Leu  Asp  Ser  Arg  Gly  Trp  Gly  Thr  Leu  Leu
          35                  40                  45

Ser  Arg  Ser  Arg  Ala  Gly  Leu  Ala  Gly  Glu  Ile  Ala  Gly  Val  Asn  Trp
     50                  55                  60

Glu  Ser  Gly  Tyr  Leu  Val  Gly  Ile  Lys  Arg  Gln  Arg  Arg  Leu  Tyr  Cys
65                       70                  75                            80

Asn  Val  Gly  Ile  Gly  Phe  His  Leu  Gln  Val  Leu  Pro  Asp  Gly  Arg  Ile
                    85                       90                       95

Ser  Gly  Thr  His  Glu  Glu  Asn  Pro  Tyr  Ser  Leu  Leu  Glu  Ile  Ser  Thr
               100                 105                      110

Val  Glu  Arg  Gly  Val  Val  Ser  Leu  Phe  Gly  Val  Arg  Ser  Ala  Leu  Phe
          115                 120                      125

Val  Ala  Met  Asn  Ser  Lys  Gly  Arg  Leu  Tyr  Ala  Thr  Pro  Ser  Phe  Gln
          130                 135                 140

Glu  Glu  Cys  Lys  Phe  Arg  Glu  Thr  Leu  Leu  Pro  Asn  Asn  Tyr  Asn  Ala
145                 150                      155                           160

Tyr  Glu  Ser  Asp  Leu  Tyr  Gln  Gly  Thr  Tyr  Ile  Ala  Leu  Ser  Lys  Tyr
                    165                      170                      175

Gly  Arg  Val  Lys  Arg  Gly  Ser  Lys  Val  Ser  Pro  Ile  Met  Thr  Val  Thr
                    180                      185                      190

His  Phe  Leu  Pro  Arg  Ile
               195
```

( 2 ) INFORMATION FOR SEQ ID NO:11:

( i ) SEQUENCE CHARACTERISTICS:
        ( A ) LENGTH: 246 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:11:

```
Met  Ala  Ala  Ala  Ile  Ala  Ser  Ser  Leu  Ile  Arg  Gln  Lys  Arg  Gln  Ala
1                   5                   10                      15

Arg  Glu  Arg  Glu  Lys  Ser  Asn  Ala  Cys  Lys  Cys  Val  Ser  Ser  Pro  Ser
          20                  25                       30

Lys  Gly  Lys  Thr  Ser  Cys  Asp  Lys  Asn  Lys  Leu  Asn  Val  Phe  Ser  Arg
          35                  40                       45

Val  Lys  Leu  Phe  Gly  Ser  Lys  Lys  Arg  Arg  Arg  Arg  Arg  Pro  Glu  Pro
     50                  55                       60

Gln  Leu  Lys  Gly  Ile  Val  Thr  Lys  Leu  Tyr  Ser  Arg  Gln  Gly  Tyr  His
65                       70                  75                            80

Leu  Gln  Leu  Gln  Ala  Asp  Gly  Thr  Ile  Asp  Gly  Thr  Lys  Asp  Glu  Asp
                    85                       90                       95

Ser  Thr  Tyr  Thr  Leu  Phe  Asn  Leu  Ile  Pro  Val  Gly  Leu  Arg  Val  Val
               100                 105                      110

Ala  Ile  Gln  Gly  Val  Gln  Thr  Lys  Leu  Tyr  Leu  Ala  Met  Asn  Ser  Glu
          115                 120                      125

Gly  Tyr  Leu  Tyr  Thr  Ser  Glu  Leu  Phe  Thr  Pro  Glu  Cys  Lys  Phe  Lys
     130                 135                      140

Glu  Ser  Val  Phe  Glu  Asn  Tyr  Tyr  Val  Thr  Tyr  Ser  Ser  Met  Ile  Tyr
145                 150                      155                           160
```

```
       Arg   Gln   Gln   Gln   Ser   Gly   Arg   Gly   Trp   Tyr   Leu   Gly   Leu   Asn   Lys   Glu
                         165                           170                           175

Gly   Glu   Ile   Met   Lys   Gly   Asn   His   Val   Lys   Lys   Asn   Lys   Pro   Ala   Ala
                         180                           185                           190

His   Phe   Leu   Pro   Lys   Pro   Leu   Lys   Val   Ala   Met   Tyr   Lys   Glu   Pro   Ser
                         195                           200                           205

Leu   His   Asp   Leu   Thr   Glu   Phe   Ser   Arg   Ser   Gly   Ser   Gly   Thr   Pro   Thr
                         210                           215                           220

Lys   Ser   Arg   Ser   Val   Ser   Gly   Val   Leu   Asn   Gly   Gly   Lys   Ser   Met   Ser
       225                           230                           235                           240

His   Asn   Glu   Ser   Thr   Thr
                         245
```

(2) INFORMATION FOR SEQ ID NO:12:

(i) SEQUENCE CHARACTERISTICS:
        (A) LENGTH: 208 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

```
       Met   Ala   Pro   Leu   Gly   Glu   Val   Gly   Asn   Tyr   Phe   Gly   Val   Gln   Asp   Ala
       1                       5                           10                          15

Val   Pro   Phe   Gly   Asn   Val   Pro   Val   Leu   Pro   Val   Asp   Ser   Pro   Val   Leu
                         20                          25                          30

Leu   Ser   Asp   His   Leu   Gly   Gln   Ser   Glu   Ala   Gly   Gly   Leu   Pro   Arg   Gly
                         35                          40                          45

Pro   Ala   Val   Thr   Asp   Leu   Asp   His   Leu   Lys   Gly   Ile   Leu   Arg   Arg   Arg
                         50                          55                          60

Gln   Leu   Tyr   Cys   Arg   Thr   Gly   Phe   His   Leu   Glu   Ile   Phe   Pro   Asn   Gly
       65                            70                          75                          80

Thr   Ile   Gln   Gly   Thr   Arg   Lys   Asp   His   Ser   Arg   Phe   Gly   Ile   Leu   Glu
                         85                          90                          95

Phe   Ile   Ser   Ile   Ala   Val   Gly   Leu   Val   Ser   Ile   Arg   Gly   Val   Asp   Ser
                         100                         105                         110

Gly   Leu   Tyr   Leu   Gly   Met   Asn   Glu   Lys   Gly   Glu   Leu   Tyr   Gly   Ser   Glu
                         115                         120                         125

Lys   Leu   Thr   Gln   Glu   Cys   Val   Phe   Arg   Glu   Gln   Phe   Glu   Glu   Asn   Trp
                         130                         135                         140

Tyr   Asn   Thr   Tyr   Ser   Ser   Asn   Leu   Tyr   Lys   His   Val   Asp   Thr   Gly   Arg
       145                           150                         155                         160

Arg   Tyr   Tyr   Val   Ala   Leu   Asn   Lys   Asp   Gly   Thr   Pro   Arg   Glu   Gly   Thr
                         165                         170                         175

Arg   Thr   Lys   Arg   His   Gln   Lys   Phe   Thr   His   Phe   Leu   Pro   Arg   Pro   Val
                         180                         185                         190

Asp   Pro   Asp   Lys   Val   Pro   Glu   Leu   Tyr   Lys   Asp   Ile   Leu   Ser   Gln   Ser
                         195                         200                         205
```

(2) INFORMATION FOR SEQ ID NO:13:

(i) SEQUENCE CHARACTERISTICS:
        (A) LENGTH: 155 amino acids
        (B) TYPE: amino acid
        (C) STRANDEDNESS: Not Relevant
        (D) TOPOLOGY: linear (ii) MOLECULE TYPE: protein ( x i ) SEQUENCE DESCRIPTION: SEQ ID NO:13:

| Met | Ala | Glu | Gly | Glu | Ile | Thr | Thr | Phe | Thr | Ala | Leu | Thr | Glu | Lys | Phe |
| 1 | | | | 5 | | | | | 10 | | | | | 15 | |

| Asn | Leu | Pro | Pro | Gly | Asn | Tyr | Lys | Lys | Pro | Lys | Leu | Leu | Tyr | Cys | Ser |
| | | | 20 | | | | | 25 | | | | | 30 | | |

| Asn | Gly | Gly | His | Phe | Leu | Arg | Ile | Leu | Pro | Asp | Gly | Thr | Val | Asp | Gly |
| | | 35 | | | | 40 | | | | | 45 | | | | |

| Thr | Arg | Asp | Arg | Ser | Asp | Gln | His | Ile | Gln | Leu | Gln | Leu | Ser | Ala | Glu |
| | 50 | | | | 55 | | | | | 60 | | | | | |

| Ser | Val | Gly | Glu | Val | Tyr | Ile | Lys | Ser | Thr | Glu | Thr | Gly | Gln | Tyr | Leu |
| 65 | | | | 70 | | | | | 75 | | | | | 80 | |

| Ala | Met | Asp | Thr | Asp | Gly | Ile | Leu | Tyr | Gly | Ser | Gln | Thr | Pro | Asn | Glu |
| | | | 85 | | | | | 90 | | | | | 95 | | |

| Glu | Cys | Leu | Phe | Leu | Glu | Arg | Leu | Glu | Glu | Asn | His | Tyr | Asn | Thr | Tyr |
| | | | 100 | | | | | 105 | | | | | 110 | | |

| Ile | Ser | Lys | Lys | His | Ala | Glu | Lys | Asn | Trp | Phe | Val | Gly | Leu | Lys | Lys |
| | | 115 | | | | 120 | | | | | 125 | | | | |

| Asn | Gly | Ser | Cys | Lys | Arg | Gly | Pro | Arg | Thr | His | Tyr | Gly | Gln | Lys | Ala |
| | 130 | | | | 135 | | | | | 140 | | | | | |

| Ile | Leu | Phe | Leu | Pro | Leu | Pro | Val | Ser | Ser | Asp |
| 145 | | | | 150 | | | | | 155 | |

( 2 ) INFORMATION FOR SEQ ID NO:14:

( i ) SEQUENCE CHARACTERISTICS:
  ( A ) LENGTH: 155 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:14:

| Met | Ala | Ala | Gly | Ser | Ile | Thr | Thr | Leu | Pro | Ala | Leu | Pro | Glu | Asp | Gly |
| 1 | | | | 5 | | | | | 10 | | | | | 15 | |

| Gly | Ser | Gly | Ala | Phe | Pro | Pro | Gly | His | Phe | Lys | Asp | Pro | Lys | Arg | Leu |
| | | | 20 | | | | | 25 | | | | | 30 | | |

| Tyr | Cys | Lys | Asn | Gly | Gly | Phe | Phe | Leu | Arg | Ile | His | Pro | Asp | Gly | Arg |
| | | 35 | | | | 40 | | | | | 45 | | | | |

| Val | Asp | Gly | Val | Arg | Glu | Lys | Ser | Asp | Pro | His | Ile | Lys | Leu | Gln | Leu |
| | 50 | | | | 55 | | | | | 60 | | | | | |

| Gln | Ala | Glu | Glu | Arg | Gly | Val | Val | Ser | Ile | Lys | Gly | Val | Cys | Ala | Asn |
| 65 | | | | 70 | | | | | 75 | | | | | 80 | |

| Arg | Tyr | Leu | Ala | Met | Lys | Glu | Asp | Gly | Arg | Leu | Leu | Ala | Ser | Lys | Cys |
| | | | 85 | | | | | 90 | | | | | 95 | | |

| Val | Thr | Asp | Glu | Cys | Phe | Phe | Phe | Glu | Arg | Leu | Glu | Ser | Asn | Asn | Tyr |
| | | | 100 | | | | | 105 | | | | | 110 | | |

| Asn | Thr | Tyr | Arg | Ser | Arg | Lys | Tyr | Thr | Ser | Trp | Tyr | Val | Ala | Leu | Lys |
| | | 115 | | | | 120 | | | | | 125 | | | | |

| Arg | Thr | Gly | Gln | Tyr | Lys | Leu | Gly | Ser | Lys | Thr | Gly | Pro | Gly | Gln | Lys |
| | 130 | | | | 135 | | | | | 140 | | | | | |

| Ala | Ile | Leu | Phe | Leu | Pro | Met | Ser | Ala | Lys | Ser |
| 145 | | | | 150 | | | | | 155 | |

( 2 ) INFORMATION FOR SEQ ID NO:15:

( i ) SEQUENCE CHARACTERISTICS:

(A) LENGTH: 194 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:15:

```
Met His Lys Trp Ile Leu Thr Trp Ile Leu Pro Thr Leu Leu Tyr Arg
 1               5                  10                  15
Ser Cys Phe His Ile Ile Cys Leu Val Gly Thr Ile Ser Leu Ala Cys
               20                  25                  30
Asn Asp Met Thr Pro Glu Gln Met Ala Thr Asn Val Asn Cys Ser Ser
           35                  40                  45
Pro Glu Arg His Thr Arg Ser Tyr Asp Tyr Met Glu Gly Gly Asp Ile
       50                  55                  60
Arg Val Arg Arg Leu Phe Cys Arg Thr Gln Trp Tyr Leu Arg Ile Asp
65                  70                  75                  80
Lys Arg Gly Lys Val Lys Gly Thr Gln Glu Met Lys Asn Asn Tyr Asn
                   85                  90                  95
Ile Met Glu Ile Arg Thr Val Ala Val Gly Ile Val Ala Ile Lys Gly
               100                 105                 110
Val Glu Ser Glu Phe Tyr Leu Ala Met Asn Lys Glu Gly Lys Leu Tyr
           115                 120                 125
Ala Lys Lys Glu Cys Asn Glu Asp Cys Asn Phe Lys Glu Leu Ile Leu
       130                 135                 140
Glu Asn His Tyr Asn Thr Tyr Ala Ser Ala Lys Trp Thr His Asn Gly
145                 150                 155                 160
Gly Glu Met Phe Val Ala Leu Asn Gln Lys Gly Ile Pro Val Arg Gly
                   165                 170                 175
Lys Lys Thr Lys Lys Glu Gln Lys Thr Ala His Phe Leu Pro Met Ala
               180                 185                 190
Ile Thr
```

(2) INFORMATION FOR SEQ ID NO:16:

(i) SEQUENCE CHARACTERISTICS:
(A) LENGTH: 215 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:16:

```
Met Gly Ser Pro Arg Ser Ala Leu Ser Cys Leu Leu Leu His Leu Leu
 1               5                  10                  15
Val Leu Cys Leu Gln Ala Gln Val Thr Val Gln Ser Ser Pro Asn Phe
               20                  25                  30
Thr Gln His Val Arg Glu Gln Ser Leu Val Thr Glu Gln Leu Ser Arg
           35                  40                  45
Arg Leu Ile Arg Thr Tyr Gln Leu Tyr Ser Arg Thr Ser Gly Lys His
       50                  55                  60
Val Gln Val Leu Ala Asn Lys Arg Ile Asn Ala Met Ala Glu Glu Gly
65                  70                  75                  80
Glu Pro Phe Ala Lys Leu Ile Val Glu Thr Glu Thr Phe Gly Ser Arg
                   85                  90                  95
Val Arg Val Arg Gly Ala Glu Thr Gly Leu Tyr Ile Gln Met Asn Lys
               100                 105                 110
```

```
Lys  Gly  Lys  Leu  Ile  Ala  Lys  Ser  Asn  Gly  Lys  Gly  Lys  Glu  Gln  Val
          115                      120                 125

Phe  Ile  Glu  Ile  Val  Leu  Glu  Asn  Asn  Tyr  Thr  Ala  Leu  Gln  Asn  Ala
     130                      135                      140

Lys  Tyr  Glu  Gly  Trp  Tyr  Met  Ala  Phe  Thr  Arg  Lys  Gly  Arg  Pro  Arg
145                      150                      155                      160

Lys  Gly  Ser  Lys  Thr  Arg  Gln  His  Gln  Arg  Glu  Val  His  Phe  Met  Lys
               165                      170                      175

Arg  Leu  Pro  Arg  Gly  His  His  Thr  Thr  Glu  Gln  Ser  Leu  Arg  Phe  Glu
               180                      185                      190

Phe  Leu  Asn  Tyr  Pro  Pro  Phe  Thr  Arg  Ser  Leu  Arg  Gly  Ser  Gln  Arg
          195                      200                      205

Thr  Trp  Ala  Pro  Glu  Pro  Arg
     210                      215
```

( 2 ) INFORMATION FOR SEQ ID NO:17:

( i ) SEQUENCE CHARACTERISTICS:
        ( A ) LENGTH: 245 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:17:

```
Met  Gly  Leu  Ile  Tyr  Leu  Leu  Leu  Ser  Leu  Leu  Glu  Pro  Ser  Tyr
1                   5                    10                      15

Pro  Thr  Thr  Gly  Pro  Gly  Thr  Arg  Leu  Arg  Arg  Asp  Ala  Gly  Gly  Arg
               20                   25                      30

Gly  Gly  Val  Tyr  Glu  His  Leu  Gly  Gly  Ala  Pro  Arg  Arg  Arg  Lys  Leu
               35                   40                      45

Tyr  Cys  Ala  Thr  Lys  Tyr  His  Leu  Gln  Leu  His  Pro  Ser  Gly  Arg  Val
     50                      55                      60

Asn  Gly  Ser  Leu  Glu  Asn  Ser  Ala  Tyr  Ser  Ile  Leu  Glu  Ile  Thr  Ala
65                      70                      75                      80

Val  Glu  Val  Gly  Gly  Val  Ala  Ile  Lys  Gly  Leu  Phe  Ser  Gly  Arg  Tyr
               85                      90                      95

Leu  Ala  Met  Asn  Lys  Arg  Gly  Arg  Leu  Tyr  Ala  Ser  Asp  His  Tyr  Asn
          100                      105                      110

Ala  Glu  Cys  Glu  Phe  Val  Glu  Arg  Ile  His  Glu  Leu  Gly  Tyr  Asn  Thr
          115                      120                      125

Tyr  Ala  Ser  Arg  Leu  Tyr  Arg  Thr  Gly  Ser  Ser  Gly  Pro  Gly  Ala  Gln
     130                      135                      140

Arg  Gln  Pro  Gly  Ala  Gln  Arg  Pro  Tyr  Tyr  Val  Ser  Val  Asn  Gly  Lys
145                      150                      155                      160

Gly  Arg  Pro  Arg  Arg  Gly  Phe  Lys  Thr  Arg  Arg  Thr  Gln  Lys  Ser  Ser
               165                      170                      175

Leu  Phe  Leu  Pro  Arg  Val  Leu  Gly  His  Lys  Asp  His  Glu  Met  Val  Arg
               180                      185                      190

Leu  Leu  Gln  Ser  Ser  Gln  Pro  Arg  Ala  Pro  Gly  Glu  Gly  Ser  Gln  Pro
          195                      200                      205

Arg  Gln  Arg  Arg  Gln  Lys  Lys  Gln  Ser  Pro  Gly  Asp  His  Gly  Lys  Met
210                      215                      220

Glu  Thr  Leu  Ser  Thr  Arg  Ala  Thr  Pro  Ser  Thr  Gln  Leu  His  Thr  Gly
225                      230                      235                      240
```

```
Gly Leu Ala Val Ala
                245
```

(2) INFORMATION FOR SEQ ID NO:18:

(i) SEQUENCE CHARACTERISTICS:
        (A) LENGTH: 269 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

```
Met Ser Leu Ser Phe Leu Leu Leu Leu Phe Phe Ser His Leu Ile Leu
 1               5                  10                  15
Ser Ala Trp Ala His Gly Glu Lys Arg Leu Ala Pro Lys Gly Gln Pro
            20                  25                  30
Gly Pro Ala Ala Thr Asp Arg Asn Pro Ile Gly Ser Ser Ser Arg Gln
                35                  40                  45
Ser Ser Ser Ser Ala Met Ser Ser Ser Ser Ala Ser Ser Ser Pro Ala
    50                  55                  60
Ala Ser Leu Gly Ser Gln Gly Ser Gly Leu Glu Gln Ser Ser Phe Gln
 65                 70                  75                  80
Trp Ser Pro Ser Gly Arg Arg Thr Gly Ser Leu Tyr Cys Arg Val Gly
                85                  90                  95
Ile Gly Phe His Leu Gln Ile Tyr Pro Asp Gly Lys Val Asn Gly Ser
                100                 105                 110
His Glu Ala Asn Met Leu Ser Val Leu Glu Ile Phe Ala Val Ser Gln
            115                 120                 125
Gly Ile Val Gly Ile Arg Gly Val Phe Ser Asn Lys Phe Leu Ala Met
130                 135                 140
Ser Lys Lys Gly Lys Leu His Ala Ser Ala Lys Phe Thr Asp Asp Cys
145                 150                 155                 160
Lys Phe Arg Glu Arg Phe Gln Glu Asn Ser Tyr Asn Thr Tyr Ala Ser
                165                 170                 175
Ala Ile His Arg Thr Glu Lys Thr Gly Arg Glu Trp Tyr Val Ala Leu
            180                 185                 190
Asn Lys Arg Gly Lys Ala Arg Lys Gly Cys Ser Pro Arg Val Lys Pro
        195                 200                 205
Gln His Ile Ser Thr His Phe Leu Pro Arg Glu Phe Lys Gln Ser Glu
210                 215                 220
Gln Pro Glu Leu Ser Phe Thr Val Thr Val Pro Glu Lys Lys Asn Pro
225                 230                 235                 240
Pro Ser Pro Ile Lys Ser Lys Ile Pro Leu Ser Ala Pro Arg Lys Asn
                245                 250                 255
Thr Asn Ser Val Lys Tyr Arg Leu Lys Phe Arg Phe Gly
                260                 265
```

(2) INFORMATION FOR SEQ ID NO:19:

(i) SEQUENCE CHARACTERISTICS:
        (A) LENGTH: 206 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

| Met | Ser | Gly | Pro | Gly | Thr | Ala | Ala | Val | Ala | Leu | Leu | Pro | Ala | Val | Leu |
|---|---|---|---|---|---|---|---|---|---|---|---|---|---|---|---|
| 1 | | | | 5 | | | | | 10 | | | | | 15 | |

Leu Ala Leu Leu Ala Pro Trp Ala Gly Trp Gly Ala Ala Ala Pro
        20              25                  30

Thr Ala Pro Asn Gly Thr Leu Glu Ala Glu Leu Glu Trp Trp Glu
        35              40                  45

Ser Leu Val Ala Leu Ser Leu Ala Trp Leu Pro Val Ala Ala Gln Pro
    50              55                  60

Lys Glu Ala Ala Val Gln Ser Gly Ala Gly Asp Tyr Leu Leu Gly Ile
65              70                  75                      80

Lys Trp Leu Trp Trp Leu Tyr Cys Asn Val Gly Ile Gly Phe His Leu
            85              90                  95

Gln Ala Leu Pro Asp Gly Trp Ile Gly Gly Ala His Ala Asp Thr Trp
        100             105                 110

Asp Ser Leu Leu Glu Leu Ser Pro Val Glu Trp Gly Val Val Ser Ile
        115             120                 125

Phe Gly Val Ala Ser Trp Phe Phe Val Ala Met Ser Ser Lys Gly Lys
    130             135                 140

Leu Tyr Gly Ser Pro Phe Phe Thr Asp Glu Cys Ile Phe Lys Glu Ile
145             150                 155                 160

Leu Leu Pro Asn Asn Tyr Asn Ala Tyr Glu Ser Tyr Lys Tyr Pro Gly
            165             170                 175

Met Phe Ile Ala Leu Ser Lys Asn Gly Lys Thr Lys Lys Gly Asn Trp
        180             185                 190

Val Ser Pro Thr Met Lys Val Thr His Phe Leu Pro Trp Leu
        195             200                 205

(2) INFORMATION FOR SEQ ID NO:20:

(i) SEQUENCE CHARACTERISTICS:
        (A) LENGTH: 198 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

Met Ser Arg Gly Ala Gly Arg Leu Gln Gly Thr Leu Trp Ala Leu Val
1               5                   10                  15

Phe Leu Gly Ile Leu Val Gly Met Val Val Pro Ser Pro Ala Gly Thr
            20                  25                  30

Arg Ala Asn Asn Thr Leu Leu Asp Ser Arg Gly Trp Gly Thr Leu Leu
        35              40                  45

Ser Arg Ser Arg Ala Gly Leu Ala Gly Glu Ile Ala Gly Val Asn Trp
    50              55                  60

Glu Ser Gly Tyr Leu Val Gly Ile Lys Arg Gln Arg Arg Leu Tyr Cys
65              70                  75                      80

Asn Val Gly Ile Gly Phe His Leu Gln Val Leu Pro Asp Gly Arg Ile
            85              90                  95

Ser Gly Thr His Glu Glu Asn Pro Tyr Ser Leu Leu Glu Ile Ser Thr
        100             105                 110

Val Glu Arg Gly Val Val Ser Leu Phe Gly Val Arg Ser Ala Leu Phe
        115             120                 125

Val Ala Met Asn Ser Lys Gly Arg Leu Tyr Ala Thr Pro Ser Phe Gln
130             135                 140

| Glu<br>145 | Glu | Cys | Lys | Phe | Arg<br>150 | Glu | Thr | Leu | Leu | Pro<br>155 | Asn | Asn | Tyr | Asn | Ala<br>160 |
| Tyr | Glu | Ser | Asp | Leu<br>165 | Tyr | Gln | Gly | Thr | Tyr<br>170 | Ile | Ala | Leu | Ser | Lys<br>175 | Tyr |
| Gly | Arg | Val | Lys<br>180 | Arg | Gly | Ser | Lys | Val<br>185 | Ser | Pro | Ile | Met | Thr<br>190 | Val | Thr |
| His | Phe | Leu | Pro | Arg<br>195 | Ile |

( 2 ) INFORMATION FOR SEQ ID NO:21:

( i ) SEQUENCE CHARACTERISTICS:
        ( A ) LENGTH: 193 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:21:

| Met<br>1 | Ala | Pro | Leu | Gly<br>5 | Glu | Val | Gly | Asn | Tyr<br>10 | Phe | Gly | Val | Gln | Asp<br>15 | Ala |
| Val | Pro | Phe | Gly<br>20 | Asn | Val | Pro | Val | Leu<br>25 | Pro | Val | Asp | Ser | Pro<br>30 | Val | Leu |
| Leu | Ser | Asp<br>35 | His | Leu | Gly | Gln | Ser<br>40 | Glu | Ala | Gly | Gly | Leu<br>45 | Pro | Arg | Gly |
| Pro | Ala<br>50 | Val | Thr | Asp | Leu | Asp<br>55 | His | Leu | Lys | Gly | Ile<br>60 | Leu | Arg | Arg | Arg |
| Gln<br>65 | Leu | Tyr | Cys | Arg | Thr<br>70 | Gly | Phe | His | Leu | Glu<br>75 | Ile | Phe | Pro | Asn | Gly<br>80 |
| Thr | Ile | Gln | Gly | Thr<br>85 | Arg | Lys | Asp | His | Ser<br>90 | Arg | Phe | Gly | Ile | Leu<br>95 | Glu |
| Phe | Ile | Ser | Ile<br>100 | Ala | Val | Gly | Leu | Val<br>105 | Ser | Ile | Arg | Gly | Val<br>110 | Asp | Ser |
| Gly | Leu | Tyr<br>115 | Leu | Gly | Met | Asn | Glu<br>120 | Lys | Gly | Glu | Leu | Tyr<br>125 | Gly | Glu | Ser |
| Lys | Leu<br>130 | Thr | Gln | Glu | Cys | Val<br>135 | Phe | Arg | Glu | Gln | Phe<br>140 | Glu | Glu | Asn | Trp |
| Tyr<br>145 | Asn | Thr | Tyr | Ser | Ser<br>150 | Asn | Leu | Tyr | Lys | His<br>155 | Val | Asp | Thr | Gly | Arg<br>160 |
| Arg | Tyr | Tyr | Val | Ala<br>165 | Leu | Asn | Lys | Asp | Gly<br>170 | Thr | Pro | Arg | Glu | Gly<br>175 | Thr |
| Arg | Thr | Lys | Arg<br>180 | His | Gln | Lys | Phe | Thr<br>185 | His | Phe | Leu | Pro | Arg<br>190 | Pro | Val |
| Asp |

( 2 ) INFORMATION FOR SEQ ID NO:22:

( i ) SEQUENCE CHARACTERISTICS:
        ( A ) LENGTH: 191 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:22:

| Met<br>1 | Ala | Glu | Gly | Glu<br>5 | Ile | Thr | Thr | Phe | Thr<br>10 | Ala | Leu | Thr | Glu | Lys<br>15 | Phe |

```
Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                      80

Ala Met Asp Thr Asp Gly Ile Leu Tyr Gly Ser Gln Thr Pro Asn Glu
                85                  90                  95

Glu Cys Ile Leu Phe Leu Glu Arg Leu Glu Glu Asn His Tyr Asn Thr
            100                 105                 110

Tyr Ile Ser Lys Lys His Ala Glu Lys Asn Trp Phe Val Gly Leu Lys
            115                 120                 125

Lys Asn Gly Ser Cys Lys Arg Gly Pro Arg Thr His Tyr Gly Gln Lys
    130                 135                 140

Ala Ile Leu Phe Leu Pro Leu Pro Val Ser Met Tyr Arg Glu Pro Ser
145                 150                 155                     160

Leu His Glu Ile Gly Glu Lys Gln Gly Arg Ser Arg Lys Ser Ser Gly
            165                 170                 175

Thr Pro Thr Met Asn Gly Gly Lys Val Val Asn Gln Asp Ser Thr
            180                 185                 190
```

( 2 ) INFORMATION FOR SEQ ID NO:23:

( i ) SEQUENCE CHARACTERISTICS:
  ( A ) LENGTH: 194 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:23:

```
Met His Lys Trp Ile Leu Thr Trp Ile Leu Pro Thr Leu Leu Tyr Arg
1               5                   10                  15

Ser Cys Phe His Ile Ile Cys Leu Val Gly Arg Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                      80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                     160

Gly Glu Met Phe Val Ala Leu Asn Gln Lys Gly Ile Pro Val Arg Gly
            165                 170                 175
```

```
Lys  Lys  Thr  Lys  Lys  Glu  Gln  Lys  Thr  Ala  His  Phe  Leu  Pro  Met  Ala
          180                      185                           190

Ile  Thr
```

(2) INFORMATION FOR SEQ ID NO:24:

(i) SEQUENCE CHARACTERISTICS:
        (A) LENGTH: 154 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:24:

```
Ala  Ala  Gly  Ser  Ile  Thr  Thr  Leu  Pro  Ala  Leu  Pro  Glu  Asp  Gly  Gly
1                   5                        10                       15

Ser  Gly  Ala  Phe  Pro  Pro  Gly  His  Phe  Lys  Asp  Pro  Lys  Arg  Leu  Tyr
               20                      25                      30

Cys  Lys  Asn  Gly  Gly  Phe  Phe  Leu  Arg  Ile  His  Pro  Asp  Gly  Arg  Val
          35                      40                      45

Asp  Gly  Val  Arg  Glu  Lys  Ser  Asp  Pro  His  Ile  Lys  Leu  Gln  Leu  Gln
     50                      55                      60

Ala  Glu  Glu  Arg  Gly  Val  Val  Ser  Ile  Lys  Gly  Val  Cys  Ala  Asn  Arg
65                       70                      75                       80

Tyr  Leu  Ala  Met  Lys  Glu  Asp  Gly  Arg  Leu  Leu  Ala  Ser  Lys  Cys  Val
               85                      90                      95

Thr  Asp  Glu  Cys  Phe  Phe  Phe  Glu  Arg  Leu  Glu  Ser  Asn  Asn  Tyr  Asn
               100                     105                    110

Thr  Tyr  Arg  Ser  Arg  Lys  Tyr  Thr  Ser  Trp  Tyr  Val  Ala  Leu  Lys  Arg
          115                     120                    125

Thr  Gly  Gln  Tyr  Lys  Leu  Gly  Ser  Lys  Thr  Gly  Pro  Gly  Gln  Lys  Ala
     130                     135                    140

Ile  Leu  Phe  Leu  Pro  Met  Ser  Ala  Lys  Ser
145                     150
```

(2) INFORMATION FOR SEQ ID NO:25:

(i) SEQUENCE CHARACTERISTICS:
        (A) LENGTH: 243 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:25:

```
Met  Ala  Ala  Ala  Ile  Ala  Ser  Ser  Leu  Ile  Arg  Gln  Lys  Arg  Gln  Ala
1                   5                        10                       15

Arg  Glu  Ser  Asn  Ser  Asp  Arg  Val  Ser  Ala  Ser  Lys  Arg  Arg  Ser  Ser
               20                      25                      30

Pro  Ser  Lys  Asp  Gly  Arg  Ser  Leu  Cys  Glu  Arg  His  Val  Leu  Gly  Val
          35                      40                      45

Phe  Ser  Lys  Val  Arg  Phe  Cys  Ser  Gly  Arg  Lys  Arg  Pro  Val  Arg  Arg
     50                      55                      60

Arg  Pro  Glu  Pro  Gln  Leu  Lys  Gly  Ile  Val  Thr  Arg  Leu  Phe  Ser  Gln
65                       70                      75                       80

Gln  Gly  Tyr  Phe  Leu  Gln  Met  His  Pro  Asp  Gly  Thr  Ile  Asp  Gly  Thr
               85                      90                      95
```

```
Lys Asp Glu Asn Ser Asp Tyr Thr Leu Phe Asn Leu Ile Pro Val Gly
            100             105                 110

Leu Arg Val Val Ala Ile Gln Gly Val Lys Ala Ser Leu Tyr Val Ala
        115             120                 125

Met Asn Gly Glu Gly Tyr Leu Tyr Ser Ser Asp Val Phe Thr Pro Glu
    130             135             140

Cys Lys Phe Lys Glu Ser Val Gly Glu Asn Tyr Tyr Val Ile Tyr Ser
145             150                 155                 160

Ser Thr Leu Tyr Arg Gln Gln Glu Ser Gly Arg Ala Trp Phe Leu Gly
                165             170                 175

Leu Asn Lys Glu Gly Gln Ile Met Lys Gly Asn Arg Val Lys Lys Thr
            180             185                 190

Lys Pro Ser Ser His Phe Val Pro Lys Pro Ile Glu Val Cys Met Tyr
        195             200                 205

Arg Glu Pro Ser Leu His Glu Ile Gly Glu Lys Gln Gly Arg Ser Arg
    210             215             220

Lys Ser Ser Gly Thr Pro Thr Met Asn Gly Gly Lys Val Val Asn Gln
225             230             235                 240

Asp Ser Thr
```